United States Patent
Kress-Spatz et al.

(10) Patent No.: US 12,400,746 B2
(45) Date of Patent: *Aug. 26, 2025

(54) SELECTIVE DISTRIBUTION OF PHARMACY ITEM DATA FROM PHARMACY ITEM TRACKING SYSTEM

(71) Applicant: Bluesight, Inc., Alexandria, VA (US)

(72) Inventors: Timothy James Leo Kress-Spatz, Arlington, VA (US); Kevin William MacDonald, Miami, FL (US); Nicholas Bastien Petersen, Washington, DC (US)

(73) Assignee: Bluesight, Inc., Alexandria, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/772,036

(22) Filed: Jul. 12, 2024

(65) Prior Publication Data

US 2025/0014700 A1  Jan. 9, 2025

Related U.S. Application Data

(63) Continuation of application No. 18/151,096, filed on Jan. 6, 2023, now Pat. No. 12,040,065, which is a
(Continued)

(51) Int. Cl.
*G16H 20/10* (2018.01)
*A61J 1/03* (2023.01)
(Continued)

(52) U.S. Cl.
CPC ............ *G16H 20/10* (2018.01); *A61J 1/03* (2013.01); *G16H 10/60* (2018.01); *G16H 40/67* (2018.01);
(Continued)

(58) Field of Classification Search
CPC ........ G16H 20/10; G16H 10/60; G16H 40/67; A61J 1/03; A61J 2205/10; A61J 2205/60
See application file for complete search history.

(56) References Cited

U.S. PATENT DOCUMENTS 4,884,827 A    12/1989  Kelley
4,961,533 A    10/1990  Teller et al.
(Continued)

FOREIGN PATENT DOCUMENTS

CA    2 722 328    10/2009
CA    2 790 220    6/2013
(Continued)

OTHER PUBLICATIONS

"AmerisourceBergen Specialty Group Reconfigures Cubixx Medical Cabinet", Jan. 9, 2011, pp. 2, <https://web.archive.org/web/20180620192642/http://pharmaceuticalcommerce.com/supply-chain-logistics/amerisourcebergen-specialty-group-reconfigures-cubixx-medical-cabinet/>.
(Continued)

*Primary Examiner* — Michael Collins
(74) *Attorney, Agent, or Firm* — Knobbe, Martens, Olson & Bear, LLP

(57) ABSTRACT

Methods and systems relate to providing varying levels of detail about a pharmacy item to a patient information system based on the capabilities of the patient information system. An intercept device can receive an identifier associated with a pharmacy item based on a scanner reading a computer-readable code. The intercept device can recognize or determine the storage capabilities or limitations of the patient information system, for example by determining various medication data fields that the patient information system uses to store pharmacy item information. The intercept device can use the machine readable code to obtain pharmacy item information that is compatible with the patient
(Continued)

information system based on those storage capabilities or limitations and can distribute that pharmacy item information to the patient information system.

20 Claims, 3 Drawing Sheets

Related U.S. Application Data continuation of application No. 16/985,594, filed on Aug. 5, 2020, now Pat. No. 11,551,797.

(60) Provisional application No. 62/883,351, filed on Aug. 6, 2019.

(51) Int. Cl.
   *G16H 10/60* (2018.01)
   *G16H 40/67* (2018.01)

(52) U.S. Cl.
   CPC ........ *A61J 2205/10* (2013.01); *A61J 2205/60* (2013.01)

(56) References Cited

U.S. PATENT DOCUMENTS

| | | |
|---|---|---|
| 5,713,485 A | 2/1998 | Liff et al. |
| 5,930,145 A | 7/1999 | Yuyama et al. |
| 5,963,134 A | 10/1999 | Bowers et al. |
| 5,986,662 A | 11/1999 | Argiro et al. |
| 6,112,502 A | 9/2000 | Frederick et al. |
| 6,249,299 B1 | 6/2001 | Tainer |
| 6,275,157 B1 | 8/2001 | Mays et al. |
| 6,294,999 B1 | 9/2001 | Yarin et al. |
| 6,330,351 B1 | 12/2001 | Yasunaga |
| 6,574,166 B2 | 6/2003 | Niemiec |
| 6,632,619 B1 | 10/2003 | Harrison et al. |
| 6,771,369 B2 | 8/2004 | Rzasa et al. |
| 6,825,864 B2 | 11/2004 | Botten et al. |
| 6,842,736 B1 | 1/2005 | Brzozowski |
| 6,847,861 B2 | 1/2005 | Lunak et al. |
| 6,851,615 B2 | 2/2005 | Jones |
| 6,861,954 B2 | 3/2005 | Levin |
| 6,877,658 B2 | 4/2005 | Raistrick et al. |
| 6,879,876 B2 | 4/2005 | O'Dougherty et al. |
| 6,900,021 B1 | 5/2005 | Harrison et al. |
| 6,933,849 B2 | 8/2005 | Sawyer |
| 6,935,560 B2 | 8/2005 | Andreasson et al. |
| 6,952,681 B2 | 10/2005 | McQuade et al. |
| 6,985,870 B2 | 1/2006 | Martucci et al. |
| 6,992,574 B2 | 1/2006 | Aupperle et al. |
| 6,994,249 B2 | 2/2006 | Peterka et al. |
| 7,036,729 B2 | 5/2006 | Chung |
| 7,061,831 B2 | 6/2006 | De La Huerga |
| 7,111,780 B2 | 9/2006 | Broussard et al. |
| 7,116,343 B2 | 10/2006 | Botten et al. |
| 7,118,029 B2 | 10/2006 | Nycz et al. |
| 7,140,542 B2 | 11/2006 | Andreasson et al. |
| 7,146,247 B2 | 12/2006 | Kirsch et al. |
| 7,151,456 B2 | 12/2006 | Godfrey |
| 7,158,030 B2 | 1/2007 | Chung |
| 7,165,077 B2 | 1/2007 | Kalies |
| 7,175,081 B2 | 2/2007 | Andreasson et al. |
| 7,177,721 B2 | 2/2007 | Kirsch et al. |
| 7,178,729 B2 | 2/2007 | Shaffer et al. |
| 7,182,256 B2 | 2/2007 | Andreasson et al. |
| 7,212,100 B2 | 5/2007 | Terenna |
| 7,212,127 B2 | 5/2007 | Jacober et al. |
| 7,227,469 B2 | 6/2007 | Varner et al. |
| 7,232,066 B2 | 6/2007 | Andreasson et al. |
| 7,253,736 B2 | 8/2007 | Tethrake et al. |
| 7,256,699 B2 | 8/2007 | Tethrake et al. |
| 7,263,501 B2 | 8/2007 | Tirinato et al. |
| 7,264,323 B2 | 9/2007 | Tainer et al. |
| 7,268,684 B2 | 9/2007 | Tethrake et al. |
| 7,275,645 B2 | 10/2007 | Mallett et al. |
| 7,299,981 B2 | 11/2007 | Hickle et al. |
| 7,316,231 B2 | 1/2008 | Hickle |
| 7,317,393 B2 | 1/2008 | Maloney |
| 7,318,529 B2 | 1/2008 | Mallett et al. |
| 7,339,550 B2 | 3/2008 | Hayama et al. |
| 7,341,147 B2 | 3/2008 | Mallett et al. |
| 7,348,884 B2 | 3/2008 | Higham |
| 7,354,884 B2 | 4/2008 | Hada et al. |
| 7,362,228 B2 | 4/2008 | Nycz et al. |
| 7,375,737 B2 | 5/2008 | Botten et al. |
| 7,394,383 B2 | 7/2008 | Hager et al. |
| 7,440,818 B2 | 10/2008 | Handfield et al. |
| 7,446,747 B2 | 11/2008 | Youngblood et al. |
| 7,454,880 B1 | 11/2008 | Austin et al. |
| 7,486,188 B2 | 2/2009 | Van Alstyne |
| 7,492,257 B2 | 2/2009 | Tethrake et al. |
| 7,492,261 B2 | 2/2009 | Cambre et al. |
| 7,504,954 B2 | 3/2009 | Spaeder |
| 7,518,502 B2 | 4/2009 | Austin et al. |
| 7,518,516 B2 | 4/2009 | Azevedo et al. |
| 7,551,089 B2 | 6/2009 | Sawyer |
| 7,559,483 B2 | 7/2009 | Hickle et al. |
| 7,564,364 B2 | 7/2009 | Zweig |
| 7,630,791 B2 | 12/2009 | Nguyen et al. |
| 7,639,136 B1 | 12/2009 | Wass et al. |
| 7,644,016 B2 | 1/2010 | Nycz et al. |
| 7,672,872 B2 | 3/2010 | Shanton |
| 7,706,915 B2 | 4/2010 | Mohapatra et al. |
| 7,706,916 B2 | 4/2010 | Hilton |
| 7,712,670 B2 | 5/2010 | Sauerwein, Jr. et al. |
| 7,715,277 B2 | 5/2010 | De La Huerga |
| 7,729,597 B2 | 6/2010 | Wright et al. |
| 7,734,157 B2 | 6/2010 | Wright et al. |
| 7,737,858 B2 | 6/2010 | Matityaho |
| 7,747,477 B1 | 6/2010 | Louie et al. |
| 7,752,085 B2 | 7/2010 | Monroe |
| 7,772,964 B2 | 8/2010 | Tethrake et al. |
| 7,775,056 B2 | 8/2010 | Lowenstein |
| 7,783,163 B2 | 8/2010 | Wright et al. |
| 7,783,174 B2 | 8/2010 | Wright et al. |
| 7,801,422 B2 | 9/2010 | Wright et al. |
| 7,815,117 B2 | 10/2010 | Tuschel et al. |
| 7,834,765 B2 | 11/2010 | Sawyer |
| 7,834,766 B2 | 11/2010 | Sawyer |
| 7,837,093 B1 | 11/2010 | Leu et al. |
| 7,837,107 B1 | 11/2010 | Leu et al. |
| 7,858,841 B2 | 12/2010 | Krautkramer et al. |
| 7,860,730 B1 | 12/2010 | Goodall et al. |
| 7,868,754 B2 | 1/2011 | Salvat, Jr. |
| 7,893,876 B2 | 2/2011 | Brown et al. |
| 7,908,030 B2 | 3/2011 | Handfield et al. |
| 7,918,830 B2 | 4/2011 | Langan et al. |
| 7,928,844 B2 | 4/2011 | Mackenzie et al. |
| 7,933,033 B2 | 4/2011 | Ohishi et al. |
| 7,976,508 B2 | 7/2011 | Hoag |
| 7,985,711 B2 | 7/2011 | Tohmatsu et al. |
| 7,990,272 B2 | 8/2011 | Wass et al. |
| 7,996,286 B2 | 8/2011 | Kreiner et al. |
| 8,002,174 B2 | 8/2011 | Coyne, III et al. |
| 8,006,903 B2 | 8/2011 | Braun et al. |
| 8,009,913 B2 | 8/2011 | Greyshock |
| 8,019,471 B2 | 9/2011 | Bogash et al. |
| 8,031,347 B2 | 10/2011 | Edwards et al. |
| 8,042,738 B2 | 10/2011 | Cloix |
| 8,049,627 B1 | 11/2011 | Addante |
| 8,063,925 B2 | 11/2011 | Tainer et al. |
| 8,065,858 B2 | 11/2011 | Leu et al. |
| 8,072,635 B2 | 12/2011 | Roberts et al. |
| 8,077,041 B2 | 12/2011 | Stern et al. |
| 8,082,192 B2 | 12/2011 | Nycz et al. |
| 8,099,339 B1 | 1/2012 | Pinsonneault et al. |
| 8,108,068 B1 | 1/2012 | Boucher et al. |
| 8,111,159 B2 | 2/2012 | Andreasson et al. |
| 8,112,175 B2 | 2/2012 | Handfield et al. |
| 8,131,397 B2 | 3/2012 | Vahlberg et al. |
| 8,154,390 B2 | 4/2012 | Heath et al. |
| 8,174,392 B1 | 5/2012 | Sagbhini et al. |

(56) References Cited

U.S. PATENT DOCUMENTS

| | | |
|---|---|---|
| 8,186,587 B2 | 5/2012 | Zmood et al. |
| 8,212,677 B2 | 7/2012 | Ferguson |
| 8,219,413 B2 | 7/2012 | Martinez et al. |
| 8,224,483 B1 | 7/2012 | Ansari et al. |
| 8,231,749 B2 | 7/2012 | Dent et al. |
| 8,258,961 B2 | 9/2012 | Phillips et al. |
| 8,261,939 B2 | 9/2012 | Knoth |
| 8,271,128 B1 | 9/2012 | Schultz |
| 8,279,069 B2 | 10/2012 | Sawyer |
| 8,283,287 B2 | 10/2012 | Aihara et al. |
| 8,284,059 B2 | 10/2012 | Ross |
| 8,285,083 B2 | 10/2012 | Canessa et al. |
| 8,285,607 B2 | 10/2012 | Danilewitz |
| 8,286,222 B2 | 10/2012 | Silverbrook et al. |
| 8,292,173 B2 | 10/2012 | Yturralde et al. |
| 8,292,186 B2 | 10/2012 | Deloche et al. |
| 8,296,950 B2 | 10/2012 | Colbrunn et al. |
| 8,313,024 B2 | 11/2012 | Marino |
| 8,319,607 B2 | 11/2012 | Grimlund et al. |
| 8,328,082 B1 | 12/2012 | Bochenko et al. |
| 8,339,649 B2 | 12/2012 | Ohishi et al. |
| 8,341,041 B2 | 12/2012 | Hull |
| 8,346,632 B2 | 1/2013 | Saghbini |
| 8,355,753 B2 | 1/2013 | Bochenko et al. |
| 8,355,962 B2 | 1/2013 | Delaney et al. |
| 8,359,338 B2 | 1/2013 | Butterfield et al. |
| 8,371,448 B1 | 2/2013 | Reaux |
| 8,376,228 B2 | 2/2013 | DeVet et al. |
| 8,384,545 B2 | 2/2013 | Hussain et al. |
| 8,385,972 B2 | 2/2013 | Bochenko et al. |
| 8,386,070 B2 | 2/2013 | Eliuk et al. |
| 8,394,053 B2 | 3/2013 | Bochenko et al. |
| 8,403,212 B2 | 3/2013 | Van Esch |
| 8,403,224 B2 | 3/2013 | Fedorko et al. |
| 8,405,508 B2 | 3/2013 | Burke |
| 8,438,067 B2 | 5/2013 | Omura et al. |
| 8,461,076 B2 | 6/2013 | Okada et al. |
| 8,483,550 B2 | 7/2013 | Wright et al. |
| 8,509,604 B2 | 8/2013 | Wright et al. |
| 8,515,251 B2 | 8/2013 | Wright et al. |
| 8,519,849 B2 | 8/2013 | Ross-Messemer |
| 8,530,379 B2 | 9/2013 | Shimizu et al. |
| 8,564,416 B2 | 10/2013 | Steven et al. |
| 8,565,552 B2 | 10/2013 | Sommer et al. |
| 8,582,171 B2 | 11/2013 | Srnka et al. |
| 8,589,271 B2 | 11/2013 | Evans |
| 8,593,278 B2 | 11/2013 | Churbock et al. |
| 8,593,678 B2 | 11/2013 | Ohishi et al. |
| D694,817 S | 12/2013 | Adam et al. |
| 8,600,548 B2 | 12/2013 | Bossi et al. |
| 8,606,596 B1 | 12/2013 | Bochenko et al. |
| 8,636,202 B2 | 1/2014 | Keefe et al. |
| 8,639,525 B2 | 1/2014 | Levine et al. |
| 8,659,395 B2 | 2/2014 | Kilian |
| 8,686,859 B2 | 4/2014 | Hussain et al. |
| 8,699,054 B2 | 4/2014 | Edwards et al. |
| 8,702,674 B2 | 4/2014 | Bochenko |
| 8,723,674 B2 | 5/2014 | Conley et al. |
| 8,749,356 B2 | 6/2014 | Hussain et al. |
| 8,755,056 B2 | 6/2014 | Edwards et al. |
| 8,825,680 B2 | 9/2014 | Burke et al. |
| 8,838,215 B2 | 9/2014 | John et al. |
| 8,868,616 B1 | 10/2014 | Otto et al. |
| 8,893,970 B2 | 11/2014 | Keefe et al. |
| 8,922,435 B2 | 12/2014 | Fontecchio et al. |
| 8,935,280 B2 | 1/2015 | Bauman et al. |
| 8,945,066 B2 | 2/2015 | Bochenko et al. |
| 8,948,478 B2 | 2/2015 | Keefe et al. |
| 8,985,388 B2 | 3/2015 | Ratnakar et al. |
| 8,990,099 B2 | 3/2015 | MacDonald et al. |
| 9,037,479 B1 | 5/2015 | MacDonald et al. |
| 9,058,412 B2 | 6/2015 | MacDonald et al. |
| 9,058,413 B2 | 6/2015 | Macdonald et al. |
| 9,058,435 B2 | 6/2015 | Keefe et al. |
| 9,171,280 B2 | 10/2015 | Gitchell et al. |
| 9,189,769 B2 | 11/2015 | Caputo et al. |
| 9,367,665 B2 | 6/2016 | MacDonald et al. |
| 9,449,296 B2 | 9/2016 | MacDonald et al. |
| 9,539,374 B2 | 1/2017 | Halpern |
| 9,582,644 B2 | 2/2017 | Gitchell et al. |
| 9,734,294 B2 | 8/2017 | MacDonald et al. |
| 9,805,169 B2 | 10/2017 | MacDonald et al. |
| 10,083,766 B2 | 9/2018 | Gitchell et al. |
| 10,210,954 B2 | 2/2019 | Caputo et al. |
| 10,600,513 B2 | 3/2020 | Gitchell et al. |
| 10,609,845 B2 | 3/2020 | Elizondo, II |
| 10,621,394 B2 | 4/2020 | Hussain et al. |
| 10,643,743 B2 | 5/2020 | Caputo et al. |
| 10,658,077 B2 | 5/2020 | Hussain et al. |
| 10,658,078 B2 | 5/2020 | Caputo et al. |
| 10,664,740 B2 | 5/2020 | Elizondo, II |
| 10,853,380 B1 | 12/2020 | Agnew et al. |
| 10,930,393 B2 | 2/2021 | Gitchell et al. |
| 11,017,352 B2 | 5/2021 | MacDonald et al. |
| 11,037,342 B1 | 6/2021 | Agnew et al. |
| 11,139,075 B2 | 10/2021 | MacDonald et al. |
| 11,551,797 B2 * | 1/2023 | Kress-Spatz ............ A61J 1/03 |
| 11,557,393 B2 | 1/2023 | Gitchell et al. |
| 11,664,105 B2 | 5/2023 | Yanowitz et al. |
| 11,907,902 B2 | 2/2024 | MacDonald et al. |
| 11,996,189 B2 | 5/2024 | MacDonald et al. |
| 12,040,065 B2 * | 7/2024 | Kress-Spatz ........... G16H 10/60 |
| 12,087,422 B2 | 9/2024 | Yanowitz et al. |
| 12,165,763 B2 | 12/2024 | Gitchell et al. |
| 2002/0026330 A1 | 2/2002 | Klein |
| 2002/0049650 A1 | 4/2002 | Reff |
| 2002/0087360 A1 | 7/2002 | Pettit |
| 2002/0087362 A1 | 7/2002 | Cobb et al. |
| 2002/0087554 A1 | 7/2002 | Seelinger |
| 2003/0055685 A1 | 3/2003 | Cobb et al. |
| 2003/0074223 A1 | 4/2003 | Hickle et al. |
| 2003/0102970 A1 | 6/2003 | Creel et al. |
| 2003/0160698 A1 | 8/2003 | Andreasson et al. |
| 2003/0216974 A1 | 11/2003 | Browne |
| 2004/0008123 A1 | 1/2004 | Carrender et al. |
| 2004/0032330 A1 | 2/2004 | Hoffman |
| 2004/0051368 A1 | 3/2004 | Caputo et al. |
| 2004/0057609 A1 | 3/2004 | Weinberg |
| 2004/0081669 A1 | 4/2004 | Greeven et al. |
| 2004/0158507 A1 | 8/2004 | Meek et al. |
| 2004/0178071 A1 | 9/2004 | Harrison et al. |
| 2004/0215486 A1 | 10/2004 | Braverman |
| 2004/0225528 A1 | 11/2004 | Brock |
| 2005/0014849 A1 | 1/2005 | Pettit et al. |
| 2005/0060171 A1 | 3/2005 | Molnar |
| 2005/0062603 A1 | 3/2005 | Fuerst et al. |
| 2005/0108044 A1 | 5/2005 | Koster |
| 2005/0125097 A1 | 6/2005 | Chudy et al. |
| 2005/0127176 A1 | 6/2005 | Dickinson |
| 2005/0149378 A1 | 7/2005 | Cyr et al. |
| 2005/0149414 A1 | 7/2005 | Schrodt et al. |
| 2005/0184151 A1 | 8/2005 | DiMaggio et al. |
| 2005/0283259 A1 | 12/2005 | Wolpow |
| 2005/0285732 A1 | 12/2005 | Sengupta et al. |
| 2005/0285746 A1 | 12/2005 | Sengupta et al. |
| 2006/0006999 A1 | 1/2006 | Walczyk et al. |
| 2006/0043177 A1 | 3/2006 | Nycz et al. |
| 2006/0043179 A1 | 3/2006 | Nycz et al. |
| 2006/0065726 A1 | 3/2006 | Andreasson et al. |
| 2006/0109105 A1 | 5/2006 | Varner et al. |
| 2006/0132311 A1 | 6/2006 | Kruest et al. |
| 2006/0145871 A1 | 7/2006 | Donati et al. |
| 2006/0152338 A1 | 7/2006 | Hsu |
| 2006/0152364 A1 | 7/2006 | Walton |
| 2006/0152367 A1 | 7/2006 | Narayanaswamy |
| 2006/0208886 A1 | 9/2006 | Beamer |
| 2006/0244593 A1 | 11/2006 | Nycz et al. |
| 2006/0267731 A1 | 11/2006 | Chen |
| 2007/0001809 A1 | 1/2007 | Kodukula et al. |
| 2007/0008399 A1 | 1/2007 | Botten et al. |
| 2007/0023512 A1 | 2/2007 | Miller et al. |
| 2007/0023513 A1 | 2/2007 | Andreasson et al. |
| 2007/0074722 A1 | 4/2007 | Giroux et al. |
| 2007/0114279 A1 | 5/2007 | Lessing et al. |

(56) References Cited

U.S. PATENT DOCUMENTS

| | | |
|---|---|---|
| 2007/0185615 A1 | 8/2007 | Bossi et al. |
| 2007/0187475 A1 | 8/2007 | MacLeod |
| 2007/0188306 A1 | 8/2007 | Tethrake et al. |
| 2007/0200702 A1 | 8/2007 | Chung |
| 2007/0213659 A1 | 9/2007 | Trovato et al. |
| 2007/0213684 A1 | 9/2007 | Hickle et al. |
| 2007/0229268 A1 | 10/2007 | Swan et al. |
| 2007/0272746 A1 | 11/2007 | Ortiz et al. |
| 2008/0004908 A1 | 1/2008 | Oh et al. |
| 2008/0012687 A1 | 1/2008 | Rubinstein |
| 2008/0045930 A1 | 2/2008 | Makin et al. |
| 2008/0046295 A1 | 2/2008 | Albrecht |
| 2008/0061153 A1 | 3/2008 | Hickle et al. |
| 2008/0094214 A1 | 4/2008 | Azevedo et al. |
| 2008/0122878 A1 | 5/2008 | Keefe et al. |
| 2008/0128482 A1 | 6/2008 | Chen et al. |
| 2008/0129496 A1 | 6/2008 | Koblasz |
| 2008/0150722 A1 | 6/2008 | Jackson |
| 2008/0157967 A1 | 7/2008 | Jones et al. |
| 2008/0172253 A1 | 7/2008 | Chung et al. |
| 2008/0186180 A1 | 8/2008 | Butler et al. |
| 2008/0191013 A1 | 8/2008 | Liberatore |
| 2008/0218307 A1 | 9/2008 | Schoettle |
| 2008/0228160 A1 | 9/2008 | Harrison |
| 2008/0231456 A1 | 9/2008 | Matityaho |
| 2008/0243088 A1 | 10/2008 | Evans |
| 2008/0270178 A1 | 10/2008 | McRae et al. |
| 2008/0296373 A1 | 12/2008 | Smood et al. |
| 2008/0297356 A1 | 12/2008 | Oberle |
| 2008/0306772 A1 | 12/2008 | Shahrokh |
| 2008/0316045 A1 | 12/2008 | Sriharto et al. |
| 2009/0002173 A1 | 1/2009 | Bergsten et al. |
| 2009/0020442 A1 | 1/2009 | Dietrich et al. |
| 2009/0058653 A1 | 3/2009 | Geissler et al. |
| 2009/0144087 A1 | 6/2009 | Kelsch et al. |
| 2009/0153290 A1 | 6/2009 | Bierach |
| 2009/0164042 A1 | 6/2009 | Handfield et al. |
| 2009/0194987 A1 | 8/2009 | Christie et al. |
| 2009/0224891 A1 | 9/2009 | Vishik et al. |
| 2009/0231138 A1 | 9/2009 | Cheung et al. |
| 2009/0267740 A1 | 10/2009 | Pizzuto et al. |
| 2009/0267772 A1 | 10/2009 | Dehnadi |
| 2009/0277815 A1 | 11/2009 | Kohl |
| 2009/0294521 A1 | 12/2009 | De La Huerga |
| 2010/0022953 A1 | 1/2010 | Bochenko et al. |
| 2010/0022987 A1 | 1/2010 | Bochenko |
| 2010/0036310 A1 | 2/2010 | Hillman |
| 2010/0036678 A1 | 2/2010 | Bray |
| 2010/0036755 A1 | 2/2010 | Saghbini |
| 2010/0042439 A1 | 2/2010 | Martinez et al. |
| 2010/0079337 A1 | 4/2010 | Hsu et al. |
| 2010/0098425 A1 | 4/2010 | Kewitsch |
| 2010/0108761 A1 | 5/2010 | Nycz et al. |
| 2010/0185458 A1 | 7/2010 | Calderwood et al. |
| 2010/0204659 A1 | 8/2010 | Bochenko |
| 2010/0217621 A1 | 8/2010 | Schoenberg et al. |
| 2010/0219097 A1 | 9/2010 | Ramasubramanian et al. |
| 2010/0238039 A1 | 9/2010 | Tethrake et al. |
| 2010/0268548 A1 | 10/2010 | Garrett et al. |
| 2010/0275625 A1 | 11/2010 | Lowenstein |
| 2010/0299158 A1 | 11/2010 | Siegel |
| 2010/0328474 A1 | 12/2010 | Hsieh |
| 2010/0332246 A1 | 12/2010 | Fedorko et al. |
| 2011/0006879 A1 | 1/2011 | Bartos |
| 2011/0060455 A1 | 3/2011 | Bogash et al. |
| 2011/0063091 A1 | 3/2011 | Kang |
| 2011/0068922 A1 | 3/2011 | Ross |
| 2011/0112682 A1 | 5/2011 | Matsukawa et al. |
| 2011/0115612 A1 | 5/2011 | Kulinets et al. |
| 2011/0125315 A1 | 5/2011 | Handfield et al. |
| 2011/0131056 A1 | 6/2011 | Chudy et al. |
| 2011/0139871 A1 | 6/2011 | Yturralde et al. |
| 2011/0161112 A1 | 6/2011 | Keefe et al. |
| 2011/0163871 A1 | 7/2011 | Einav et al. |
| 2011/0166878 A1 | 7/2011 | Louie et al. |
| 2011/0184751 A1 | 7/2011 | Holmes |
| 2011/0187549 A1 | 8/2011 | Balasing |
| 2011/0202174 A1 | 8/2011 | Bogash et al. |
| 2011/0225100 A1 | 9/2011 | Sangal et al. |
| 2011/0227722 A1 | 9/2011 | Salvat, Jr. |
| 2011/0240729 A1 | 10/2011 | Schuck |
| 2011/0257991 A1 | 10/2011 | Shukla |
| 2011/0270441 A1 | 11/2011 | Handfield et al. |
| 2011/0291809 A1 | 12/2011 | Niemiec et al. |
| 2011/0301446 A1 | 12/2011 | Kamen |
| 2011/0313395 A1 | 12/2011 | Krulevitch et al. |
| 2012/0037266 A1 | 2/2012 | Bochenko |
| 2012/0041778 A1 | 2/2012 | Kraft |
| 2012/0044054 A1 | 2/2012 | Hussain et al. |
| 2012/0061463 A1 | 3/2012 | Burke |
| 2012/0089411 A1 | 4/2012 | Srnka et al. |
| 2012/0089418 A1 | 4/2012 | Kamath et al. |
| 2012/0116798 A1 | 5/2012 | Heath et al. |
| 2012/0125994 A1 | 5/2012 | Heath et al. |
| 2012/0130534 A1 | 5/2012 | Wurm |
| 2012/0173440 A1 | 7/2012 | Becker et al. |
| 2012/0179132 A1 | 7/2012 | Valk et al. |
| 2012/0185951 A1 | 7/2012 | Bauman et al. |
| 2012/0209619 A1 | 8/2012 | Knotts et al. |
| 2012/0240067 A1 | 9/2012 | Bauman et al. |
| 2012/0273087 A1 | 11/2012 | Einy et al. |
| 2012/0278096 A1 | 11/2012 | Holness |
| 2012/0278228 A1 | 11/2012 | Rubinstein |
| 2012/0323208 A1 | 12/2012 | Bochenko et al. |
| 2012/0325330 A1 | 12/2012 | Prince et al. |
| 2013/0018356 A1 | 1/2013 | Prince et al. |
| 2013/0038452 A1 | 2/2013 | Sawyer |
| 2013/0041784 A1 | 2/2013 | Danilewitz |
| 2013/0092727 A1 | 4/2013 | Edwards et al. |
| 2013/0105568 A1 | 5/2013 | Jablonski et al. |
| 2013/0151005 A1 | 6/2013 | Gerold et al. |
| 2013/0191149 A1 | 7/2013 | Kolberg et al. |
| 2013/0197927 A1 | 8/2013 | Vanderveen et al. |
| 2013/0218329 A1 | 8/2013 | Henderson et al. |
| 2013/0221082 A1 | 8/2013 | Botten |
| 2013/0225945 A1 | 8/2013 | Prince et al. |
| 2014/0060729 A1 | 3/2014 | Srnka et al. |
| 2014/0066880 A1 | 3/2014 | Prince et al. |
| 2014/0114472 A1 | 4/2014 | Bossi et al. |
| 2014/0117081 A1 | 5/2014 | Jablonski et al. |
| 2014/0136229 A1 | 5/2014 | Levine et al. |
| 2014/0142975 A1 | 5/2014 | Keefe et al. |
| 2014/0184390 A1 | 7/2014 | Elizondo, II |
| 2014/0184391 A1 | 7/2014 | Elizondo, II |
| 2014/0197954 A1 | 7/2014 | Caputo et al. |
| 2014/0210596 A1 | 7/2014 | Hussain et al. |
| 2014/0262919 A1 | 9/2014 | Hussain et al. |
| 2014/0263614 A1 | 9/2014 | Keefe et al. |
| 2014/0276213 A1 | 9/2014 | Bochenko |
| 2014/0282197 A1 | 9/2014 | Keefe et al. |
| 2014/0291397 A1 | 10/2014 | Caputo et al. |
| 2014/0367080 A1 | 12/2014 | Hussain et al. |
| 2015/0058182 A1 | 2/2015 | Kress-Spatz et al. |
| 2017/0109497 A1 | 4/2017 | Tribble et al. |
| 2018/0247703 A1 | 8/2018 | D'Amato |
| 2019/0088354 A1 | 3/2019 | Yanowitz et al. |
| 2019/0272396 A1 | 9/2019 | Clouser et al. |
| 2019/0304583 A1 | 10/2019 | Henderson et al. |
| 2020/0013494 A1 | 1/2020 | Caputo et al. |
| 2020/0167534 A1 | 5/2020 | Elizondo, II |
| 2021/0319872 A1 | 10/2021 | Valentine |
| 2022/0282199 A1 | 9/2022 | Vann |
| 2024/0346446 A1 | 10/2024 | MacDonald et al. |

FOREIGN PATENT DOCUMENTS

| | | |
|---|---|---|
| CN | 102791310 B | 12/2014 |
| DE | 10 2006 028 736 | 4/2007 |
| EP | 2 496 283 | 9/2012 |
| IN | 2012/04914 P4 | 10/2013 |
| WO | WO 02/095675 | 11/2002 |
| WO | WO 03/071943 | 9/2003 |
| WO | WO 2006/026246 | 3/2006 |
| WO | WO 2006/135830 | 12/2006 |

(56) References Cited

FOREIGN PATENT DOCUMENTS

| WO | WO 2010/074781 | 7/2010 |
|---|---|---|
| WO | WO 2011/056888 | 9/2011 |
| WO | WO 2011/115676 | 9/2011 |
| WO | WO 2011/150013 | 12/2011 |
| WO | WO 2013/082423 | 6/2013 |
| WO | WO 2013/116873 | 8/2013 |
| WO | WO 2013/134256 | 9/2013 |
| WO | WO 2014/159928 | 10/2014 |
| WO | WO 2014/189834 | 11/2014 |
| WO | WO 2015/026387 | 2/2015 |

OTHER PUBLICATIONS

Bacheldor, Beth, "ASD Healthcare Deploys RFID Refrigerated Drug Cabinets", RFID Journal, Sep. 24, 2007, p. 1. <http://www.rfidjournal.com/articles/view?3632>.
Bacheldor, Beth, "Cardinal Health Readies Item-Level Pilot", RFID Journal, May 31, 2006, p. 1. <http://www.rfidjournal.com/articles/view?2380>.
Bacheldor, Beth, "UCSD Medical Center Expands Its RFID Deployment", RFID Journal, Oct. 29, 2008, pp. 2. <http://www.rfidjournal.com/articles/view?4423>.
Bacheldor, Beth, "UMass Med Center Finds Big Savings Through Tagging", RFID Journal, Nov. 21, 2007, pp. 2. <http://www.rfidjournal.com/articles/view?3763/2>.
Barlas, Stephen, "Pharmacy Product Tracing Likely to Go National—Costs to Pharmacies Worrisome," Pharmacy & Therapeutics, Jan. 2009, vol. 34 No. 1, p. 14.
Baum, "How did RFID help University of MD Medical Center cut medication error rate?" Med City News, https://medcitynews.com/2013/12/rfid-help-university-md-medical-center-cut-medication-error-rate/?rf=1, Dec. 4, 2013, 2 Pages.
Becker et al., "SmartDrawer: RFID-Based Smart Medicine Drawer for Assistive Environments", Conference: Proceedings of the 2nd International Conference on Pervasive Technologies Related to Assistive Environments, PETRA 2009, Corfu, Greece, Jun. 9-13, 2009, pp. 8.
Belson, D., "Storage, Distribution, and Dispensing of Medical Supplies," Create Interim Report Under FEMA Grant EMW-2004-GR-0112, Apr. 21, 2005, pp. 1-36.
Bendavid et al., "Using RFID to Improve Hospital Supply Chain Management for High Value and Consignment Items", Procedia Computer Science, vol. 5, 2011, pp. 849-856.
Bendavid et al., "Redesigning the Replenishment Process of Medical Supplies in Hospitals with RFID", Business Process Management Journal, 2010, vol. 16, No. 6, pp. 991-1013.
Brown, Dennis E., "RFID Implementation", McGraw-Hill Communications, 2007, Ch. 3 & 7 (portions), pp. 62-65, 81, 92-96, 106-113, 188-193 & 429.
Bryant, Blake, "Hacking SIEMs to Catch Hackers: Decreasing the Mean Time to Respond to Network Security Events with a Novel Threat Ontology in SIEM Software", Master's Thesis, University of Kansas, 2016, pp. 257.
Çakici et al., "Using RFID for the Management of Pharmaceutical Inventory-System Optimization and Shrinkage Control," Decision Support Systems, 2011, pp. 842-852.
Cangialosi et al., "Leveraging RFID in Hospitals: Patient Life Cycle and Mobility Perspectives", IEEE Applications & Practice, Sep. 2007, pp. 18-23.
Chao et al., "Determining Technology Trends and Forecasts of RFID by a Historical Review and Bibliometric Analysis from 1991 to 2005", Technovation, vol. 27, 2007, pp. 268-279.
Collins, "RFID Cabinet Manages Medicine", RFID Journal, Aug. 12, 2004, p. 1. <http://www.rfidjournal.com/articles/pdf?1081>.
CPG Sec. 400.210, Radiofrequency Identification Feasibility Studies and Pilot Programs for Drugs Nov. 2004 Compliance Policy Guide available at: <http://www.fda.gov/ICECI/ComplianceManuals/CompliancePolicyGuidanceManual/ucm074357.htm>.
"Crash Cart Inventory Checklist", Outpatient Surgery Magazine, Oct. 2004, p. 1. <http://www.outpatientsurgery.net/resources/forms/2004/pdf/OutpatientSurgeryMagazine_0410_crashCart.pdf>.
Curtin et al., "Making the 'Most' out of RFID: a research agenda for the study of the adoption, usage and impact of RFID," Information Technology Management, Apr. 2007, pp. 87-110.
"Data Gathering Developments", Manufacturing Chemist, Feb. 1, 2005, p. 24. <https://www.manufacturingchemist.com/news/article_page/Data_gathering_developments/35805>.
Dutta et al., "RFID and Operations Management: Technology, Value, and Incentives", Production and Operations Management (POMS), vol. 16, No. 5, Sep.-Oct. 2007, pp. 646-655.
Edwards, John, "RFID Smart Shelves and Cabinets", RFID Journal, Aug. 24, 2009, pp. 4. <http://www.rfidjournal.com/articles/view?5140/4>.
*Electric Power Group v. Alstom, S.A.*, 830 F.3d 1350, 1353-54, 119 USPQ2d 1739, 1741-42 (Fed. Cir. 2016), pp. 12.
Epstein et al., "Development of a Scheduled Drug Diversion Surveillance System Based on an Analysis of Atypical Drug Transactions", Anesthesia and Analgesia, Oct. 2007, vol. 105, No. 4, pp. 1053-1060.
Erdem et al., "Investigation of RFID Tag Readability for Pharmaceutical Products at Item Level", Drug Development and Industrial Pharmacy, 2009, vol. 35, No. 11, pp. 1312-1324.
Fahrni, Jerry, "More RFID Refrigerator Stuff—Cubixx and myCubixx", Sep. 3, 2012, pp. 4. <http://jerryfahrni.com/2012/09/more-rfid-refrigerator-stuff-cubixx-and-mycubixx/>.
"Faraday Cage", Wikipedia, last edited Apr. 12, 2018, pp. 5. <https://en.wikipedia.org/wiki/Faraday_cage>.
Floerkemeier et al., "The Smart Box Concept for Ubiquitous Computing Environments", The Smart Box Concept for Ubiquitous Computing Environments, 2004, pp. 4.
Garza, Anyssa, "The Future of Pharmacy Medication Kit Storage", Pharmacy Times, https://www.pharmacytimes.com/contributor/anyssa-garza/2014/12/the-future-of-pharmacy-medication-kit-storage, Dec. 12, 2014, 2 Pages.
Glover et al., "RFID Essentials", O'Reilly Media, 2006, pp. 2, 14, 24, 31, 33, 107-110, 113-114, 117, 137-143, 162-169, 178-179.
Gonzalez, Stephanie, "Health Maintenance System (HMS) Hardware Research, Design, and Collaboration," NASA USRP—Internship Final Report, 2010, pp. 1-20.
Green, Kathryn, "Doing the Wave: Inventory Management with RFID", Diagnostic & Interventional Services, UMass Memorial Medical Center, Worcester, MA, vol. 15, No. 9, Sep. 2007, pp. 7. <https://www.cathlabdigest.com/articles/Doing-Wave-Inventory-Management-RFID>.
Harrop et al., "RFID for Healthcare and Pharmaceuticals, 2008-2018," Securing Pharma, May 2008, pp. 1-12.
Hawkins-Simons, "RFID Streamlines Refilling of Drug Trays", Pharmacy Technology Report, https://www.pharmacypracticenews.com/Pharmacy-Technology-Report/Article/03-14/RFID-Streamlines-Refilling-of-Drug-Trays/26159, Mar. 21, 2014, 9 Pages.
Ho et al., "A Prototype on RFID and Sensor Networks for Elder Healthcare: Progress Report", SIGCOMM '05 Workshops, Aug. 22-26, 2005, Philadelphia, PA, pp. 70-75.
Houliston, Bryan, "Integrating RFID Technology into a Drug Administration System," Bulletin of Applied Computing and Information Technology, vol. 3, No. 1, May 2005, pp. 8. Retrieved Sep. 26, 2013 from <http://citrenz.ac.nz/bacit/0301/2005Houliston_RFID.htm>.
Howard, JD, "Implementation of RFID in the Pharmaceutical Industry", Advisor: Dr. Jay Singh, California Polytechnic State University, San Luis Obispo, CA, Feb. 2009, pp. 11.
Humble, RN, Carol, "How RFID Freed Nurses From the Pain of Inventory Duties", Cath Lab Digest, Dec. 2009, vol. 17, No. 12. <https://www.cathlabdigest.com/articles/How-RFID-Freed-Nurses-From-Pain-Inventory-Duties>.
"Intel & Siemens Launch RFID Blood Bank in Malaysia", RFID Journal, Aug. 16, 2007, p. 1. <https://www.rfidjournal.com/articles/view?6801>.
Jones et al., "The Benefits, Challenges and Impacts of Radio Frequency Identification Technology (RFID) for Retailers in the UK", Marketing Intelligence & Planning, Mar. 2005, vol. 23, No. 4, pp. 395-402.

(56) References Cited

OTHER PUBLICATIONS

Jorgensen et al., "Executable Use Cases: Requirements for a Pervasive Health Care System," IEEE Software, Mar./Apr. 2004, pp. 34-41.
Juels, Ari, "RFID Security and Privacy: A Research Survey", IEEE Journal on Selected Areas in Communications, vol. 24, No. 2, Feb. 2006, pp. 381-394.
Kinsella, Bret, "Premier, Inc. Identifies Kit Check as 'Technology Breakthrough Product'—Awards exclusive agreement for pharmacy kit medication tracking solution", Press Release, https://kitcheck.com/2014/04/premier-inc-identifies-kit-check-technology-breakthrough-product-awards-exclusive-agreement-pharmacy-kit-medication-tracking-solution/, Apr. 2, 2014, 5 Pages.
KitCheck, Bluesight for Controlled Substances Overview, as retrieved Aug. 30, 2018 from https://web.archive.org/web/20180830001131/https://kitcheck.com/learn-more/video/bluesight-for-controlled-substances-overview/ in 1 page.
KitCheck, Diversion Events, as retrieved Aug. 30, 2018 from https://web.archive.org/web/20180830001851/https://kitcheck.com/solutions/controlled-substances/diversion-events/ in 3 pages.
KitCheck, "PharMEDium Prefilled Syringes with Kit Check: ASHP Symposium Summary", Jun. 2016, <https://kitcheck.com/wp-content/uploads/2016/06/pharmedium-prefilled-syringes-with-kit-check-download.pdf> in 9 pages.
KitCheck, Security, as retrieved Aug. 30, 2018 from https://web.archive.org/web/20180830000040/https://kitcheck.com/security/ in 1 page.
KitCheck, "St. Rita's Medical Center: 75% First-year ROI, Less Frustration", Case Study, 2016, <https://kitcheck.com/learn-more/case-study/st-ritas-medical-center/> in 2 pages.
Lahtela et al., "RFID and NFC in Healthcare: Safety of Hospitals Medication Care", 2008 Second International Conference on Pervasive Computing Technologies for Healthcare, Tampere, Finland, Jan. 30-Feb. 1, 2008, pp. 4.
Lai et al., "Enhancing Medication Safety and Reduce Adverse Drug Events on Inpatient Medication Administration using RFID," WSEAS Transactions on Communications, Oct. 2008, vol. 7, No. 10, pp. 1045-1054.
Lampe et al., "The Smart Box Application Model," Advances in Pervasive Computing, 2004, pp. 1-6.
Lewis, Mark O., "RFID-Enabled Capabilities and their Impact on Healthcare Process Performance", 31st International Conference on Information Systems, St. Louis, 2010, pp. 1-20.
Liu et al., "Point-of-Care Support for Error-Free Medication Process" (Jun. 25, 2007), retrieved Aug. 21, 2017, 12 pages, available at http://ieeexplore.ieee.org/document/4438162/.
McCall et al., "RMAIS: RFID-based Medication Adherence Intelligence System" (Aug. 31, 2010), retrieved Aug. 21, 2017, 4 pages, available at http://ieeexplore.ieee.org/document/5627529/.
"McKesson's Announces New Touch-Screen Driven Medication Dispensing Solution", Business Wire, Jun. 15, 2009, pp. 2, Available at: <http://www.businesswire.com/news/home/20090615005349/en/Mckesson-Announces-Touch-Screen-Driven-Medication-Dispensing-Solution#.VR7quPnF_10>.
"Medical Packaging Inc. Announces Clear Stem Flag Label System for Ampoules, Vials, and Syringes" Feb. 1, 2006 available at: <http://www.medpak.com/v1/news/20060201_CSFLAG.pdf>, in 1 page.
"Medication Tray Management" Pharmacy Purchasing & Products, Feb. 2018, pp. 18 & 20.
"Medication Tray Management" Pharmacy Purchasing & Products, Presentation, Nov. 2018, pp. 76 & 78.
"Medication Tray Management" Pharmacy Purchasing & Products, State of Pharmacy Automation, Aug. 2016, pp. 42 & 45.
"Medication Tray Management" Pharmacy Purchasing & Products, State of Pharmacy Automation, Aug. 2019, pp. 34-35.
Mehrjerdi, Yahia Zare, "RFID-Enabled Healthcare Systems: Risk-Benefit Analysis", International Journal of Pharmaceutical and Healthcare Marketing, 2010, vol. 4, No. 3, pp. 282-300.

Meiller et al., "Adaptive Knowledge-Based System for Health Care Applications with RFID-Generated Information", Decision Support Systems, vol. 51, 2011, pp. 198-207.
Mowry, Mike, "A Survey of RFID in the Medical Industry: With Emphasis on Applications to Surgery and Surgical Devices", MAE188, Introduction to RFID, Dr. Rajit Gadh, UCLA, Jun. 9, 2008, pp. 22.
"New RFID Medical Cabinets Deployed at 50 Hospitals", RFID Journal, Sep. 17, 2007, pp. 2. <https://www.rfidjournal.com/articles/view?6823>.
New et al., "Utilize ADC Transaction Data to Detect Diversion", Oct. 2017, vol. 14, No. 10, pp. 3, as retrieved from https://www.pppmag.com/article/2119/.
O'Connor, Mary Catherine, "Drug Distributor Uses RFID to Vend Meds", RFID Journal, May 23, 2006, pp. 2. <https://www.rfidjournal.com/articles/view?2363/2>.
O'Connor, Mary Catherine, "GlaxoSmithKline Tests RFID on HIV Drug", RFID Journal, Mar. 24, 2006, pp. 2. <https://www.rfidjournal.com/articles/view?2219/>.
O'Connor, Mary Catherine, "Interrogators Start to Evolve", RFID Journal, Jun. 1, 2006, pp. 3. <http://www.rfidjournal.com/purchase-access?type=Article&id=2398&r=%2Farticles%2Fview%3F2398>.
O'Connor, Mary Catherine, "Johnson & Johnson Finds Value in Multiple RFID Apps", RFID Journal, Apr. 23, 2008, pp. 2. <http://www.rfidjournal.com/articles/pdf?4046>.
O'Connor, Mary Catherine, "McKesson Starts RFID Pilot for Viagra", RFID Journal, Feb. 17, 2005, pp. 2. <http://www.rfidjournal.com/articles/view?2157>.
O'Connor, Mary Catherine, "Pfizer Using RFID to Fight Fake Viagra", RFID Journal, Jun. 6, 2006, pp. 2. <http://www.rfidjournal.com/articles/pdf?2075>.
O'Connor, Mary Catherine, "To Keep Drugs from Expiring, Hospital Tests Intelliguard System", RFID Journal, Jan. 12, 2011, pp. 3. <http://www.rfidjournal.com/articles/view?8123>.
"ODIN Innovation Lab: EasyTunnel RFID", as posted Jul. 13, 2009, archived via archive.org <https://web.archive.org/web/20200316173502/https://www.youtube.com/watch?v=0rQhT4sIQnw>, 1 page.
"ODIN RFID HQ Tour 2009", as posted Mar. 19, 2009, archived via archive.org <https://web.archive.org/web/20200316180429/https://www.youtube.com/watch?v=4Y4XIID0B_Y>, 1 page.
O'Driscoll et al., "RFID: An Ideal Technology for Ubiquitous Computing?" Dublin Institute of Technology School of Electronic and Communications Conference Papers, Jan. 1, 2008, pp. 1-17.
Pace et al., "Distributed Ambulatory Research in Therapeutics Network (DARTNet): Summary Report", Effective Health Care Research Reports, No. 14, Agency for Healthcare Research and Quality, Jul. 2009, pp. 41.
Pappu, Ph.D. et al., "RFID in Hospitals: Issues and Solutions" Consortium for the Accelerated Deployment of RFID in Distribution, Sep. 2004, pp. 1-12.
Parida et al., "Application of RFID Technology for In-House Drug Management System", 15th International Conference on Network-Based Information Systems, 2012, pp. 577-581.
"RFID Medical Cabinets Evaluated in New Benchmark", RFID Journal, Sep. 12, 2007, pp. 2. <http://www.rfidjournal.com/articles/view?6819>.
Roberti, Mark, "RFID Basics for Health Care", RFID in Health Care, Produced by RFID Journal, Sep. 17, 2009, The Westin Waltham-Boston, Waltham, MA, p. 33.
Saygin, C., "Adaptive Inventory Management Using RFID Data", The International Journal of Advanced Manufacturing Technology, 2007, vol. 32, pp. 1045-1051.
Singh et al., "Versatility of Radio Frequency Identification (RFID) Tags in the Pharmaceutical Industry", Instrumentation Science and Technology, vol. 36, pp. 656-663, 2008.
Summerfield, et al. "Evaluation of Medication Kit Processing Time Using Radio Frequency Identification (RFID) Technology", Innovations in Pharmacy, 2015, vol. 6, No. 2, Article 199, 7 Pages.
Swedberg, Claire, "North Carolina Hospital Identifies Recalled Drugs Via RFID", RFID Journal, http://www.rfidjournal.com/articles/view?10913, Aug. 14, 2013, 4 Pages.

(56) References Cited

OTHER PUBLICATIONS

Swedberg, Claire, "Tennessee Hospital Tracks High-Value Items", RFID Journal, Aug. 5, 2009, pp. 2. <http://www.rfidjournal.com/articles/view?5106>.
Swedberg, Claire, "Zimmer Ohio to Use RFID to Manage Orthopedic Products", RFID Journal, May 12, 2010, pp. 3. <https://www.rfidjournal.com/articles/pdf?7588>.
Tsai et al., "iMAT: Intelligent Medication Administration Tools" (Jul. 1, 2010), retrieved Aug. 21, 2017, 8 pages, available at http://ieeexplore.ieee.org/document/5556551/.
Tsai et al., "Smart Medication Dispenser: Design, Architecture and Implementation" (Sep. 27, 2010), retrieved Aug. 21, 2017, 12 pages, available at http://ieeexplore.ieee.org/document/5585838/.
Tzeng et al., "Evaluating the Business Value of RFID: Evidence from Five Case Studies," International Journal of Production Economics, 2008, vol. 112, pp. 601-613.
"UPM Raflatac UHF EPC Gen2 RFID in ODIN Solution at Johnson-Johnson DePuyIn-Q-Tel", as posted Jun. 10, 2009, archived via archive.org <https://web.archive.org/web/20200316174347/https://www.youtube.com/watch?v=JWGyR8Bgfl8>, 1 page.
"Vizient, Inc. Awards Kit Check Contract for Pharmacy Kit Medication Inventory Tracking and Replenishment", Press Release, http://www.prweb.com/releases/2016/09/prweb13691526.htm, Sep. 19, 2016, 3 Pages.
Wang et al., "Applying RFID Technology to Develop a Distant Medical Care Service Platform," International Journal of Electronic Business Management, 2010, vol. 8, No. 2, pp. 161-170.
Wang et al., "RFID Applications in Hospitals: A Case Study on a Demonstration RFID Project in a Taiwan Hospital", Proceedings of the 39th Hawaii International Conference on System Sciences, 2006, pp. 1-10.
Wasserman, Elizabeth, "Purdue Pharma to Run Pedigree Pilot", RFID Journal, May 31, 2005, pp. 2. <http://www.rfidjournal.com/articles/view?1626>.
Complaint, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Dec. 1, 2017, 45 pages.
Exhibit L; Fagron Academy, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Dec. 1, 2017, 2 pages.
Defendant's Answer, Affirmative Defenses and Counterclaims to Plaintiff's Complaint, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805, 169), Case No. 2:17-cv-01041-ALM-CMV (S.D. Ohio), Jan. 2, 2018, 43 pages.
Plaintiff's Answer to Defendant's Counterclaims, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jan. 19, 2018, 14 pages.
Plaintiff Kit Check, Inc.'s Motion to Strike Insufficient Defenses, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jan. 19, 2018, 8 pages.
Defendant's First Amended Answer, Affirmative Defenses and Counterclaims to Plaintiff's Complaint, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Feb. 9, 2018, 43 pages.
Defendant'Memorandum in Opposition to Plaintiff Kit Check, Inc.'s Motion to Strike Insufficient Defenses, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Feb. 9, 2018, 6 pages.
Plaintiff's Answer to Defendant's First Amended Counterclaims, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Feb. 21, 2018, 14 pages.
Plaintiff Kit Check, Inc.'s Reply in Support of its Motion to Strike Insufficient Defenses, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Feb. 21, 2018, 6 pages.
Defendant Health Care Logistics, Inc.'s Motion for Judgment on the Pleadings Pursuant to Fed. R. Civ. P. 12(C), *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), May 25, 2018, 31 pages.
Exhibit A; U.S. Pat. No. 8,990,099, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), May 25, 2018, 12 pages.
Opinion & Order, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jun. 13, 2018, 9 pages.
Defendant Health Care Logistics, Inc's Invalidity Contentions Pursuant to Local Patent Rule 103.4, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jun. 18, 2018, 25 pages.
Exhibit 1; Initial Invalidity Claim Chart for U.S. Pat. No. 8,990,099, *Kit Check, Inc. v. Health Care Logistics, Inc.*, Case No. 2:17-cv-01041-ALM-CMV (S.D. Ohio), Jun. 18, 2018, 51 pages.
Exhibit 2; Initial Invalidity Claim Chart for U.S. Pat. No. 9,058,413, *Kit Check, Inc. v. Health Care Logistics, Inc.*, Case No. 2:17-cv-01041-ALM-CMV (S.D. Ohio), Jun. 18, 2018, 94 pages.
Exhibit 3; Initial Invalidity Claim Chart for U.S. Pat. No. 9,058,412, *Kit Check, Inc. v. Health Care Logistics, Inc.*, Case No. 2:17-cv-01041-ALM-CMV (S.D. Ohio), Jun. 18, 2018, 83 pages.
Exhibit 4; Initial Invalidity Claim Chart for U.S. Pat. No. 9,734,294, *Kit Check, Inc. v. Health Care Logistics, Inc.*, Case No. 2:17-cv-01041-ALM-CMV (S.D. Ohio), Jun. 18, 2018, 58 pages.
Exhibit 5; Initial Invalidity Claim Chart for U.S. Pat. No. 9,805,169, *Kit Check, Inc. v. Health Care Logistics, Inc.*, Case No. 2:17-cv-01041-ALM-CMV (S.D. Ohio), Jun. 18, 2018, 251 pages.
Exhibit 6; Initial Invalidity Claim Chart for U.S. Pat. No. 9,037,479, *Kit Check, Inc. v. Health Care Logistics, Inc.*, Case No. 2:17-cv-01041-ALM-CMV (S.D. Ohio), Jun. 18, 2018, 43 pages.
Exhibit 7; Initial Invalidity Claim Chart for U.S. Pat. No. 9,367,665, *Kit Check, Inc. v. Health Care Logistics, Inc.*, Case No. 2:17-cv-01041-ALM-CMV (S.D. Ohio), Jun. 18, 2018, 109 pages.
Plaintiff Kit Check, Inc.'s Memorandum in Opposition to Defendant Health Care Logistics, Inc.'s Motion for Judgment on the Pleadings, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jun. 29, 2018, 35 pages.
Exhibit 1; Non-Final Office Action for U.S. Pat. No. 8,990,099, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jun. 29, 2018, 11 pages.
Exhibit 2; Notice of Allowance for U.S. Pat. No. 8,990,099, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jun. 29, 2018, 15 pages.
Exhibit 3; Non-Final Office Action for U.S. Pat. No. 9,367,665, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jun. 29, 2018, 12 pages.

(56) References Cited

OTHER PUBLICATIONS

Exhibit 4; Response to Non-Final Office Action for U.S. Pat. No. 9,367,665, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jun. 29, 2018, 18 pages.
Defendant Health Care Logistics, Inc.'s Reply in Support of Motion for Judgment on the Pleadings Pursuant To Fed. R. Civ. P. 12(C), *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jul. 20, 2018, 22 pages.
Exhibit A, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jul. 20, 2018, 43 pages.
Exhibit B; Plaintiff Kit Check, Inc.'s Disclosure of Asserted Claims and Infringement Contentions under Local Patent Rule 103.2, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jul. 20, 2018, 11 pages.
Plaintiff Kit Check, Inc.'s Motion to Strike Portions of Defendants' Reply or, in the Alternative, Motion for Leave to File a Sur-Reply, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Aug. 10, 2018, 6 pages.
Exhibit A; Plaintiff Kit Check, Inc.'s Sur-Reply in Opposition to Defendant's Motion for Judgment on the Pleadings, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Aug. 10, 2018, 5 pages.
Defendant Health Care Logistics, Inc.'s Memorandum In Opposition to Plaintiff Kit Check, Inc.'s Motion to Strike Portions of Defendant's Reply or, in the Alternative, Motion for Leave to File a Sur-Reply, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Aug. 31, 2018, 6 pages.
Plaintiff Kit Check, Inc.'s Reply in Support of its Motion to Strike Portions of Defendant's Reply or, in the Alternative, Motion for Leave to File a Sur-Reply, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Sep. 14, 2018, 7 pages.
Joint Claim Construction and Prehearing Statement, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Sep. 20, 2018, 21 pages.
Plaintiff Kit Check, Inc.'s Opening Claim Construction Brief, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Nov. 16, 2018, 50 pages.
Exhibit 1; Disputed Claim Terms Chart, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Nov. 16, 2018, 4 pages.
Declaration of Jeffrey Fischer, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Nov. 16, 2018, 24 pages.
Defendant Health Care Logistics, Inc.'s Opening Claim Construction Brief, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Nov. 16, 2018, 32 pages.
Exhibit 1002; File History of U.S. Pat. No. 9,367,665, *Health Care Logistics, Inc.* v. *Kit Check, Inc.*, Case No. PGR2019-00022, Nov. 30, 2018, 256 pages.
Exhibit 1003; Expert Declaration, *Health Care Logistics, Inc.* v. *Kit Check, Inc.*, Case No. PGR2019-00022, Nov. 30, 2018, 9 pages.
Exhibit 1013; Claim Construction Brief (Defendant), *Health Care Logistics, Inc.* v. *Kit Check, Inc.*, Case No. PGR2019-00022, Nov. 30, 2018, 32pages.
Exhibit 1014; Claim Construction Brief (Plaintiff), *Health Care Logistics, Inc.* v. *Kit Check, Inc.*, Case No. PGR2019-00022, Nov. 30, 2018, 50 pages.
Petition for Inter Partes Review of U.S. Pat. No. 8,990,099, *Health Care Logistics, Inc.* v. *Kit Check, Inc.*, Case No. IPR2019-00376, Nov. 30, 2018, 42 pages.
Exhibit 1002; File History of U.S. Pat. No. 8,990,099, *Health Care Logistics, Inc.* v. *Kit Check, Inc.*, Case No. IPR2019-00376, Nov. 30, 2018, 557 pages.
Exhibit 1003; Expert Declaration, *Health Care Logistics, Inc.* v. *Kit Check, Inc.*, Case No. IPR2019-00376, Nov. 30, 2018, 9 pages.
Exhibit 1010; Claim Construction Brief (Defendant), *Health Care Logistics, Inc.* v. *Kit Check, Inc.*, Case No. IPR2019-00376, Nov. 30, 2018, 32 pages.
Exhibit 1011; Claim Construction Brief (Plaintiff), *Health Care Logistics, Inc.* v. *Kit Check, Inc.*, Case No. IPR2019-00376, Nov. 30, 2018, 50 pages.
Petition for Inter Partes Review of U.S. Pat. No. 9,058,412, *Health Care Logistics, Inc.* v. *Kit Check, Inc.*, Case No. IPR2019-00385, Nov. 30, 2018, 75 pages.
Exhibit 1002; File History of U.S. Pat. No. 9,058,412, *Health Care Logistics, Inc.* v. *Kit Check, Inc.*, Case No. IPR2019-00385, Nov. 30, 2018, 75 pages.
Exhibit 1003; Expert Declaration, *Health Care Logistics, Inc.* v. *Kit Check, Inc.*, Case No. IPR2019-00385, Nov. 30, 2018, 9 pages.
Exhibit 1013; Claim Construction Brief (Defendant), *Health Care Logistics, Inc.* v. *Kit Check, Inc.*, Case No. IPR2019-00385, Nov. 30, 2018, 32 pages.
Exhibit 1014; Claim Construction Brief (Plaintiff), *Health Care Logistics, Inc.* v. *Kit Check, Inc.*, Case No. IPR2019-00385, Nov. 30, 2018, 50 pages.
Petition for Inter Partes Review of U.S. Pat. No. 9,058,413, *Health Care Logistics, Inc.* v. *Kit Check, Inc.*, Case No. IPR2019-00387, Dec. 1, 2018, 73 pages.
Exhibit 1002; File History of U.S. Pat. No. 9,058,413, *Health Care Logistics, Inc.* v. *Kit Check, Inc.*, Case No. IPR2019-00387, Dec. 1, 2018, 549 pages.
Exhibit 1003; Expert Declaration, *Health Care Logistics, Inc.* v. *Kit Check, Inc.*, Case No. IPR2019-00387, Dec. 1, 2018, 9 pages.
Exhibit 1009; Children's Hospital Boston Joins Others Using RFID to Track Implantables, *Health Care Logistics, Inc.* v. *Kit Check, Inc.*, Case No. IPR2019-00387, Dec. 1, 2018, 3 pages.
Exhibit 1012; The "Orange Book", *Health Care Logistics, Inc.* v. *Kit Check, Inc.*, Case No. IPR2019-00387, Dec. 1, 2018, 1103 pages.
Exhibit 1013; Claim Construction Brief (Defendant), *Health Care Logistics, Inc.* v. *Kit Check, Inc.*, Case No. IPR2019-00387, Dec. 1, 2018, 32 pages.
Exhibit 1014; Claim Construction Brief (Plaintiff), *Health Care Logistics, Inc.* v. *Kit Check, Inc.*, Case No. IPR2019-00387, Dec. 1, 2018, 50 pages.
Petition for Inter Partes Review of U.S. Pat. No. 9,805,169, *Health Care Logistics, Inc.* v. *Kit Check, Inc.*, Case No. IPR2019-00388, Dec. 1, 2018, 76 pages.
Exhibit 1002; File History of U.S. Pat. No. 9,805,169, *Health Care Logistics, Inc.* v. *Kit Check, Inc.*, Case No. IPR2019-00388, Dec. 1, 2018, 286 pages.
Exhibit 1003; Expert Declaration, *Health Care Logistics, Inc.* v. *Kit Check, Inc.*, Case No. IPR2019-00388, Dec. 1, 2018, 9 pages.
Exhibit 1009; Claim Construction Brief (Defendant), *Health Care Logistics, Inc.* v. *Kit Check, Inc.*, Case No. IPR2019-00388, Dec. 1, 2018, 32 pages.

(56) References Cited

OTHER PUBLICATIONS

Exhibit 1010; Claim Construction Brief (Plaintiff), *Health Care Logistics, Inc. v. Kit Check, Inc.*, Case No. IPR2019-00388, Dec. 1, 2018, 50 pages.
Petition for Inter Partes Review of U.S. Pat. No. 9,367,665, *Health Care Logistics, Inc. v. Kit Check, Inc.*, Case No. IPR2019-00394, Dec. 3, 2018, 69 pages.
Exhibit 1002; File History of U.S. Pat. No. 9,367,665, *Health Care Logistics, Inc. v. Kit Check, Inc.*, Case No. IPR2019-00394, Dec. 3, 2018, 256 pages.
Exhibit 1003; Expert Declaration, *Health Care Logistics, Inc. v. Kit Check, Inc.*, Case No. IPR2019-00394, Dec. 3, 2018, 9 pages.
Exhibit 1013; Claim Construction Brief (Defendant), *Health Care Logistics, Inc. v. Kit Check, Inc.*, Case No. IPR2019-00394, Dec. 3, 2018, 32 pages.
Exhibit 1014; Claim Construction Brief (Plaintiff), *Health Care Logistics, Inc. v. Kit Check, Inc.*, Case No. IPR2019-00394, Dec. 3, 2018, 50 pages.
Plaintiff Kit Check, Inc.'s Notice of Filing Deposition Transcript of Jeffrey Fischer, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jan. 3, 2019, 3 pages.
Exhibit A; Deposition of Jeffrey Fischer, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jan. 3, 2019, 86 pages.
Plaintiff Kit Check, Inc.'s Responsive Claim Construction Brief, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jan. 3, 2019, 23 pages.
Exhibit A, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jan. 3, 2019, 43 pages.
Exhibit B; Deposition of Jeffrey Fischer, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jan. 3, 2019, 22 pages.
Defendant Health Care Logistics, Inc.'s Response to Plaintiff Kit Check, Inc.'s Opening Claim Construction Brief, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jan. 3, 2019, 22 pages.
Plaintiff Kit Check, Inc.'s Memorandum in Opposition to Defendant Health Care Logistics, Inc.'s Motion for Stay, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Feb. 11, 2019, 21 pages.
Exhibit 1; Defendant Health Care Logistics, Inc.'s Invalidity Contentions Pursuant to Local Patent Rule 103.4, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Feb. 11, 2019, 26 pages.
Defendant Health Care Logistics, Inc.'s Reply in Support of Motion for Stay, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Feb. 25, 2019, 10 pages.
Patent Owner's Preliminary Response, *Health Care Logistics, Inc. v. Kit Check, Inc.*, Case No. IPR2019-00376, U.S. Pat. No. 8,990,099, Mar. 8, 2019, 26 pages.
Patent Owner's Preliminary Response, *Health Care Logistics, Inc. v. Kit Check, Inc.*, Case No. IPR2019-00385, U.S. Pat. No. 9,058,412 B2, Mar. 8, 2019, 28 pages.

Patent Owner's Preliminary Response, *Health Care Logistics, Inc. v. Kit Check, Inc.*, Case No. IPR2019-00387, U.S. Pat. No. 9,058,413 B2, Mar. 13, 2019, 28 pages.
Patent Owner's Preliminary Response, *Health Care Logistics, Inc. v. Kit Check, Inc.*, Case No. IPR2019-00388, U.S. Pat. No. 9,805,169 B2, Mar. 13, 2019, 25 pages.
Patent Owner's Preliminary Response, *Health Care Logistics, Inc. v. Kit Check, Inc.*, Case No. IPR2019-00394, U.S. Pat. No. 9,367,668 B2, Mar. 13, 2019, 28 pages.
Opinion & Order, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Mar. 14, 2019, 17 pages.
Joint Stipulation of Partial Dismissal Without Prejudice, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Apr. 16, 2019, 2 pages.
Transcript of Markman Hearing Proceedings, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), May 6, 2019, 74 pages.
Decision Denying Institution of Inter Partes Review 35 U.S.C. § 314, *Health Care Logistics, Inc. v. Kit Check, Inc.*, Case No. IPR2019-00385, U.S. Pat. No. 9,058,412 B2, Jun. 3, 2019, 28 pages.
Decision Denying Institution of Inter Partes Review 35 U.S.C. § 314, *Health Care Logistics, Inc. v. Kit Check, Inc.*, Case No. IPR2019-00385, U.S. Pat. No. 9,805,169 B2, Jun. 3, 2019, 20 pages.
Decision Denying Institution of Inter Partes Review 35 U.S.C. § 314, *Health Care Logistics, Inc. v. Kit Check, Inc.*, Case No. IPR2019-00376, U.S. Pat. No. 8,990,099 B2, Jun. 4, 2019, 18 pages.
Decision Denying Institution of Inter Partes Review 35 U.S.C. § 314, *Health Care Logistics, Inc. v. Kit Check, Inc.*, Case No. IPR2019-00387, U.S. Pat. No. 9,058,413 B2, Jun. 7, 2019, 26 pages.
Decision Denying Institution of Inter Partes Review 35 U.S.C. § 314, *Health Care Logistics, Inc. v. Kit Check, Inc.*, Inc., Case No. IPR2019-00394, U.S. Pat. No. 9,367,665 B2, Jun. 11, 2019, 25 pages.
Stipulation and [Proposed] Order Granting Leave to Amend Plaintiff's Infringement Contentions and Defendant's Invalidity Contentions, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jul. 3, 2019, 3 pages.
Defendant Health Care Logistics, Inc.'s Motion for Leave to File Second Amended Answer, Affirmative Defenses, and Counterclaims, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jul. 17, 2019, 5 pages.
Exhibit A; Defendant's Second Amended Answer, Affirmative Defenses, and Counterclaims to Plaintiff's Complaint, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jul. 17, 2019, 49 pages.
Request for Ex Parte Reexamination Under 35 U.S.C. 302-307 and 37 C.F.R. 1.510, U.S. Pat. No. 8,990,099 B2, U.S. Appl. No. 13/554,342, filed Jul. 25, 2019 in 80 pages.
Request for Ex Parte Reexamination Under 35 U.S.C. 302-307 and 37 C.F.R. 1.510, U.S. Pat. No. 9,058,412 B2, U.S. Appl. No. 14/603,730, filed Jul. 26, 2019 in 118 pages.
Request for Ex Parte Reexamination Under 35 U.S.C. 302-307 and 37 C.F.R. 1.510, U.S. Pat. No. 9,058,413 B2, U.S. Appl. No. 14/603,828, filed Jul. 25, 2019 in 151 pages.
Request for Ex Parte Reexamination Under 35 U.S.C. 302-307 and 37 C.F.R. 1.510, U.S. Pat. No. 9,805,169 B2, U.S. Appl. No. 14/701,958, filed Jul. 26, 2019 in 220 pages.
Request for Ex Parte Reexamination Under 35 U.S.C. 302-307 and 37 C.F.R. 1.510, U.S. Pat. No. 9,367,665 B2, U.S. Appl. No. 14/818,113, filed Jul. 26, 2019 in 164 pages.

(56) References Cited

OTHER PUBLICATIONS

Opinion & Order, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Aug. 30, 2019, 26 pages.

* cited by examiner

SELECTIVE DISTRIBUTION OF PHARMACY ITEM DATA FROM PHARMACY ITEM TRACKING SYSTEM

CROSS-REFERENCE TO RELATED APPLICATIONS

This application is a continuation of U.S. patent application Ser. No. 18/151,096, entitled "SELECTIVE DISTRIBUTION OF PHARMACY ITEM DATA FROM PHARMACY ITEM TRACKING SYSTEM," filed on Jan. 6, 2023, which is a continuation of U.S. patent application Ser. No. 16/985,594, entitled "SELECTIVE DISTRIBUTION OF PHARMACY ITEM DATA FROM PHARMACY ITEM TRACKING SYSTEM," filed on Aug. 5, 2020, which claims priority benefit to U.S. Provisional Application No. 62/883,351, entitled "SELECTIVE DISTRIBUTION OF PHARMACY ITEM DATA FROM PHARMACY ITEM TRACKING SYSTEM," filed Aug. 6, 2019, each of which is hereby incorporated herein by reference in its entirety. Any and all applications for which a foreign or domestic priority claim is identified in the Application Data Sheet as filed with the present application are incorporated by reference under 37 CFR 1.57 and made a part of this specification.

BACKGROUND

Tracking the location, status, and/or other information regarding individual items is often beneficial. Such tracking can often be complex, as in some applications the number of individual items to be tracked can be thousands, millions, or more. As one example, in a healthcare facility, pharmacy items, such as, medications, drugs, diluents, medical and surgical supplies, gauze, scissors, needles, labels, baggies, bandages, packaging, vials, syringes, and/or other medical items for which a pharmacy is responsible, that are distributed from the pharmacy should be managed closely to conform to regulatory guidelines regarding use and waste, to avoid misadministration and diversion, and to ensure appropriate inventory management and patient billing. As another example, shipping and receiving operations process many individual items per day, routing them through various preparation, packaging, routing, shipping, and delivery stages.

DETAILED DESCRIPTION

Figure 1:
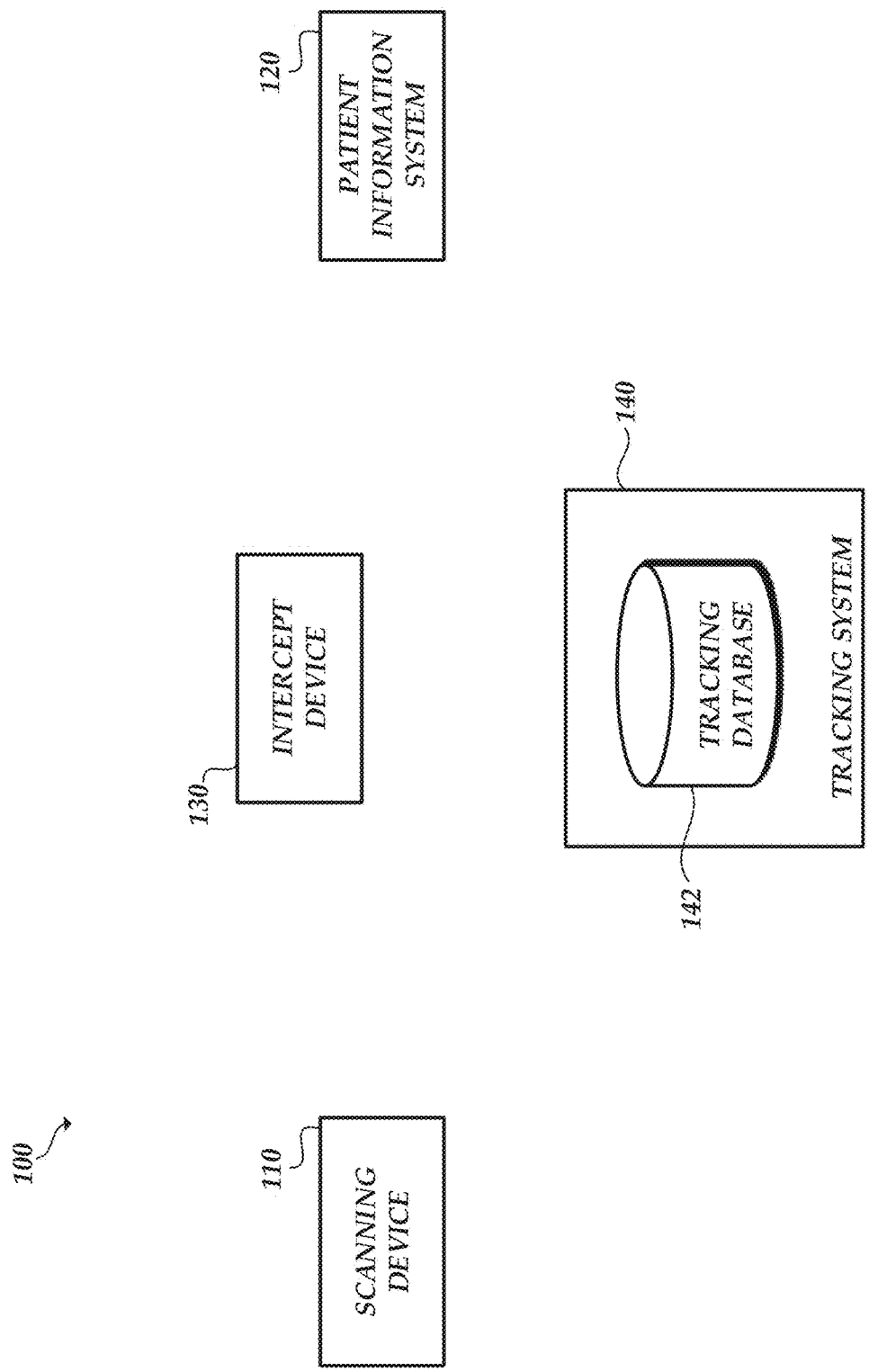
FIG. 1 is a block diagram illustrating an environment for tracking items and/or selectively communicating medication data field values to a patient information system.

Systems and methods are described herein for tracking individual items and/or selectively distributing data associated with individual items. Although various aspects of the disclosure will be described with regard to examples and embodiments, one skilled in the art will appreciate that the disclosed embodiments and examples should not be construed as limiting.

In the present disclosure, reference is made to items. As used herein, the term "item" is used broadly to define any article, person, process, or procedure that may be tracked using a tracking system. In some examples described herein, an item can be a pharmacy item.

The term "pharmacy item" is used broadly to refer to any item that is distributed from a pharmacy or otherwise used in the medical treatment of a patient in a healthcare facility. By way of non-limiting example, a pharmacy item can be a medication, drug, diluent, or other medical or surgical supply, including gauze, scissors, needles, syringes, labels, baggies, bandages, medical packaging, vials or other medical containers, or any other healthcare item. Throughout this disclosure, examples are described wherein a pharmacy item is a medication, or dose thereof, to be administered to a patient; however, these examples are not intended to be limiting, and a pharmacy item can be a non-medication healthcare item used in the treatment of a patient. However, a pharmacy item is merely a subset of the items contemplated within this application and tracking of other types of items, in other contexts, is also within the scope of this disclosure. For example, an item may refer to any package or product processed in manufacturing operation, shipping and receiving operation, storage operation, etc. Moreover, in some instances, the term item is used broadly to encompass tracking of people or animals. For example, the tracking systems described herein may be used to track a patient or healthcare professional within a healthcare facility. In some instances, item may refer to a process or procedure. For example, in the healthcare context, an item may refer to a particular test prescribed for a particular patient.

In some instances, items can contain or be associated with one or more machine-readable codes or labels, for example, barcodes (e.g., but not limited to, one-dimensional barcodes, two-dimensional barcodes, such as, QR codes, etc.), radio-frequency identification (RFID) tags, etc. For example, individual items can include a code or an RFID tag having machine-readable information such as an item identifier, intended user, or location, for example. A container such as a box, tray, or canister that includes pharmacy items can include a code or an RFID tag having machine-readable information such as a kit identifier, kit type, intended user, or location, for example.

A machine-readable code, label, or tag can include an identifier that corresponds to a particular patient with whom the item(s) is/are associated. The machine-readable code can include identifiers that correspond to product identifiers (e.g., National Drug Codes (NDC) or Universal Product Code (UPC)), lot numbers, and expiration dates. The identifiers can correspond to medications listed in a pharmacy item order, such as, NDC. In some instances, identifiers can correspond to one or more unique identifiers associated with the pharmacy items or doses thereof, which are generated by a tracking system and used to track the pharmacy item. A pharmacist or other user can verify the contents of a pharmacy item for accuracy. The identifiers or other information can be associated with the code or RFID tags in a computer database to allow subsequent identification and processing by RFID or other technology.

As used herein, the term "unique identifier" or similar term, is intended to refer to an identifier, such as an alphanumeric identifier, that can uniquely identify an item from other items. In some cases, a unique identifier can uniquely identify an item from other items that include the same type of drug or from other items that include the same drug. In some cases, a unique identifier can uniquely identify an item from all other items. For example, an NDC is used to identify different drugs and a UPC is used to identify different products. However, an NDC is unable to identify a particular vial, syringe, bag, or dose, of one type of drug from a different vial, syringe, bag, or dose, of the same kind of drug. Similarly, a UPC is unable to identify one instance of a product from another instance of the same product. The unique identifier, however, can uniquely identify a particular vial, syringe, bag, or dose from all other vials, syringes, bags, or doses of a particular drug and other drugs or pharmacy items, and in some cases, may also be referred to as a universally unique identifier or item-specific unique identifier. Further, the unique identifier can be embedded in a machine-readable label, which may also be referred to herein as a machine-readable unique identifier. In some cases, the unique identifier only uniquely identifies an associated item within the tracking system.

A pharmacy item can be released to the healthcare facility to be administered to the patient. In some instances, the pharmacy item is released to a nursing station or other pharmacy item drop off location within a healthcare facility. From the nursing station or other pharmacy item drop off location, the pharmacy item can be picked up by a nurse, a doctor, or other healthcare professional and delivered and administered to the patient. In some instances, custody of the pharmacy item is handed off between various healthcare professionals multiple times after being received in the healthcare facility but before arriving at the patient. For this reason, it can be difficult to track a pharmacy item throughout the entire process of entry, preparation, and delivery and administration to the patient. The methods and systems described herein can allow for increased accuracy in tracking the pharmacy item in these circumstances.

When the pharmacy item is to be administered to the patient, the administering healthcare professional can scan one or more of the machine-readable labels printed on or associated with the pharmacy item. The healthcare professional can also scan one or more machine-readable codes or labels associated with the patient, for example a patient identifier encoded within a machine-readable label, which can be located on a wristband on the patient. In some instances, by scanning both a machine-readable code or label associated with a pharmacy item and a machine-readable label associated with the particular patient, the system can verify that the pharmacy item can be administered to that particular patient. For example, the system can verify that the item being administered is not expired, past its beyond-use date, or recalled/blacklisted.

Embodiments of the system described herein can be used to track items from preparation, delivery, and/or other processing steps. In some instances, the systems and methods described herein can be used to track the location and/or other status of particular items.

In some instances, at the various stages in the preparation and delivery process, machine-readable unique identifiers can be scanned to indicate particular actions, for example, arrival at a particular location, custody exchange, or administration to a patient. When scanned, a pharmacy item tracking system can update the tracking database entries to include additional information provided by the scan. For example, once the pharmacy item is delivered to a nursing station, a machine-readable unique identifier associated with the pharmacy item can be scanned to indicate that the pharmacy item has reached the nursing station. When a particular nurse, picks up the pharmacy item for delivery to the patient the pharmacy item can be scanned again and the tracking database entry can be updated to include information about which nurse has taken custody of the pharmacy item. When the pharmacy item is delivered to the patient, the machine-readable unique identifier associated with a particular pharmacy item can be scanned to indicate that the particular pharmacy item has been (or is about to be) administered to a patient. When the pharmacy item or a portion thereof is leftover, the machine-readable unique identifier associated with a particular pharmacy item can be scanned to indicate that the particular pharmacy item has been (or is about to be) returned or disposed of.

In some instances, the systems and methods as described herein can be integrated into existing systems without requiring modification of the existing systems. For example, the systems and methods described herein can intercept communication between existing hardware at the facility, parse the communication to extract item information therefrom, obtain unique identifiers associated with the item, and generate and/or update tracking database entries associated with the item, while maintaining the expected communication between existing healthcare facility hardware.

Although the preceding description has outlined an example of a tracking system at a healthcare facility and used to track pharmacy items, it will be appreciated that the tracking system need not be limited to such an application. For example, the tracking systems as described herein can be used within a healthcare facility to track non-pharmacy items. For instance, the tracking systems may be used in a healthcare facility to track wheelchairs, beds, food orders, etc. Moreover, the tracking systems can be used to track patients themselves, or to track a patient's progress through various stages of treatment. Further, the tracking systems may be used to track patient samples, for example, tissue samples, blood samples, etc., as they are processed. The tracking systems described herein also have wide applicability in non-healthcare applications. For example, the tracking systems can be employed in manufacturing operations, shipping and receiving operations, warehouse and storage operations, etc. For example, the tracking system can be used to track individual component parts as they are assembled in manufacturing process, individual packages to be shipped in a distribution network, or the location and movement of individual items within a warehouse.

In some cases, where the items to be tracked are already associated with codes that identify them uniquely, the tracking systems and methods described herein may make use of these existing codes. For example, in a hospital a patient may be assigned a unique patient code during intake. A machine-readable label including the embedded unique patient code may be affixed to the patient, for example, with a wristband. Hospital procedures may require scanning of the machine-readable label at various stages of the patient's treatment, for example, before administering medication to the patient. When the machine-readable label is scanned, information from the scan may be sent to a hospital system for processing, for example, to determine whether the medication about to be administered is recalled, past it's beyond use date, or recalled/blacklisted. The tracking system described herein can intercept this transmission, create and/or modify tracking database entries, for example, by updating an entry related to the patient's location, and then retransmit the information to the existing hospital system. Accordingly, the tracking system is able to provide additional tracking functionality using existing unique codes and machine-readable labels, without disrupting the functionality of the existing hospital systems. By co-opting existing unique codes and machine-readable labels where available, the tracking systems described herein are able to overload those codes or labels with additional tracking information.

Systems and methods will now be described in greater detail, by way of example, in reference to several embodiments shown in the figures.

Intercept Device

As described herein, a pharmacy item can include a machine readable code that can be scanned by the scanning device. In some cases, the scanning device scans the machine readable code of the pharmacy item and communicates machine readable data to a patient information system, such as an electronic medical records (EMR) computer. The patient information system can receive and store the machine readable data. In addition, the patient information system can utilize the machine readable data to lookup additional data in another database. For example, the patient information system may be able to use the database to translate a specific drug associated with the machine readable data (for example, Tylenol) into a generic drug (for example, acetaminophen).

Embodiment disclosed herein provide systems, methods, and apparatuses for implementing an intercept device to enable tracking of pharmacy items and/or selective distribution of data associated with those pharmacy items to the patient information system. The intercept device can recognize or determine the storage capabilities or limitations of the patient information system. For example, the intercept device can determine which categories of data that the patient information system uses to store pharmacy item information. And the intercept device can use the machine readable code to obtain pharmacy item information that is compatible with the patient information system based on those storage capabilities or limitations, and can distribute that pharmacy item information to the patient information system. In this way, the patient information system receives its pharmacy item information from the intercept device, without performing its own data lookup. In addition to reducing the amount of computing resources or computing time utilized by the patient information system, in some cases the intercept device has access to pharmacy item information that would otherwise be unavailable to the patient information system. This can improve the safety of the patient information system, for example, by identifying pharmacy items that are expired or recalled. Thus, the implementation of the disclosed intercept device can advantageously improve the robustness of information of the patient information system. In addition, by identifying the capabilities of the patient information system and providing it with mostly (or, in some cases, only) those categories of information that are compatible with its capabilities, the intercept device streamlines and reduces a likelihood of error during data distribution. Furthermore, in some cases, an intercept device can be integrated into an existing healthcare system, thereby limiting costs associated with a system replacement.

An intercept device can act as an intermediary between a scanning device and a patient information system by receiving an identifier from the scanning device and distributing data to the patient information system. For example, the intercept device can receive an identifier associated with a pharmacy item from a scanning device. The intercept device can use the identifier to gather medication data field values for the particular pharmacy item and then can distribute some or all of those medication data field values to the patient information system. By providing the patient information system with medication data field values (instead of, or in addition to, the identifier received from the scanning device), the intercept device advantageously reduces the processing and/or tasks required by the patient information system, since the patient information system does not need to perform its own data lookup using the identifier.

Furthermore, in some instances, the intercept device can determine which medication data fields the patient information system uses to store medication data field values. For example, the intercept device can query the patient information system to determine which medication data fields that the patient information system uses to store information. As another example, the intercept device can determine the medication data fields, based on the type, manufacturer, version or other information about the patient information system. In some cases, this information may be stored in a lookup table. The intercept device can then distribute those medication data field values (and, in some cases, only those medication data fields) that the patient information system is configured to store. In this way, the intercept device provides the patient information system with information that the patient information system is configured to store (e.g., based on the capabilities of the patient information system). In some cases, intercept device distributes one or more medication data field values that the patient information system is not configured to store. In some such cases, the patient information system can ignore or regard some or all of those medication data field values, or can create additional data fields for those medication data field values.

Environment Overview

FIG. 1 is a block diagram illustrating an environment 100 for tracking items and/or selectively communicating medication data field values to a patient information system 120. In the illustrated embodiment, the environment 100 includes a scanning device 110, a patient information system 120, an intercept device 130, and a tracking system 140. The tracking system 140 includes a tracking database 142. Fewer or more devices or systems can be used in the environment 100 as desired.

Some or all of the scanning device 110, the patient information system 120, the intercept device 130, or the tracking system 140 can be communicatively coupled, for example, via a wired or wireless network. The network can include a local area network, for example, a private network, or a wide area network, including, for example, the Internet. In certain embodiments, some or all of the scanning device 110, the patient information system 120, the intercept device 130, or the tracking system 140 can form part of a single device and communicate via a computer bus. Regardless of the configuration, each separate device can include one or more processors and a computer-readable medium that stores specific computer-executable instructions for carrying out the operations described herein.

The scanning device 110 can be any device configured to scan machine-readable codes, labels, or tags and retrieve machine-readable data therefrom. For example, the scanning device 110 can be an RFID reader or RFID reading station. As another example, the scanning device 110 can include a barcode reader. For example, the scanning device 110 can include a one-dimensional barcode reader or a two-dimensional barcode reader, such as a QR code reader. The scanning device 110 can include a light source, such as a laser, that emits light and a light detector, such as a photodiode, to detect light reflected from the barcode or other machine-readable code. The scanning device 110 can use the detected light to determine the machine-readable data from the barcode or other machine-readable code. In certain embodiments, the scanning device 110 can include an image sensor, such as a charge-coupled device (CCD) image sensor or a complementary metal-oxide semiconductor (CMOS) image sensor. The image sensor can capture an image of the barcode or other machine-readable code, and the scanning device 110 can parse the captured image to extract the machine-readable data. The scanning device 110 can include an RFID tag reader. For example, the scanning device 110 can include or control an antenna that emits a radio frequency signal, which causes an RFID tag to respond with machine-readable data. The machine-readable data can be used to track an item at various preparation, transport, or other processing stages, or a set of items at various preparation, transport, or other processing stages.

The machine-readable data can include any type of data, such as a unique identifier, generic identifier, National Drug Code (NDC), Universal Product Number (UPC), patient data, drug data, etc. In some instances, the scanning device 110 can include a communication interface whereby the scanning device 110 can communicate the machine-readable data to other devices in the environment 100, such as, the patient information system 120 or the intercept device 130. The communication interface may allow the scanning device 110 to communicate wireless or via a wired connection.

In some instances, the scanning device 110 can be associated with a particular person. For example, the scanning device 110 can be associated with a healthcare professional, such as a nurse or doctor. In some instances, the scanning device 110 can be associated with a particular location. For example, the scanning device 110 can be associated with a processing station, a nursing station, or patient's room. In some instances, the scanning device 110 may not be associated with a particular location or person. Rather, machine-readable codes can be associated with locations or people and used to associate particular scans with particular locations or people.

As an example, a scanning device 110 at a nursing station can scan a machine-readable code or label that includes an embedded unique identifier associated with an item. The scanning device 110 can interpret machine-readable data (which can include, for example, the unique identifier) from the machine-readable code or label. This data can be sent to a tracking system and used to indicate that the item has been received at the nursing station.

As another example, a particular nurse or other healthcare professional can scan a machine-readable code including a unique identifier associated with an item to indicate that the particular nurse or other healthcare professional is taking custody of the item (e.g., to deliver the item to the patient), or to indicate that the particular dose is being administered to the patient, etc.

The patient information system 120 can include a computing device used to enter, generate, receive, and/or otherwise process an item. The patient information system 120 can be implemented as personal computer, including a desktop or laptop, a tablet, a mobile phone, or other portable computing device. The computing device can be implemented as a server, or similar networked processing device, that receives and processes an item entered by a remote user. The patient information system 120 can include a computer-readable medium storing computer executable instructions that when executed, enable a computing device to generate, receive, and/or process the item. In some cases, the patient information system 120 can communicate with a printer to print a label or tag for an item, or print an item order. For example, the patient information system 120 can generate a print file, which is sent to the printer and the printer can print the label, tag, or item order based on the print file.

The patient information system 120 can include a database such as a database for electronic medical records (EMRs). EMRs can be a digital version of the paper charts in the clinician's office, or can include patient data, medical history data, treatment history data, or the like.

The database can store, or be configured to store, medication data field values that correspond to a particular set of medication data fields (sometimes referred to as categories of data). The medication data fields can include, but are not limited to, drug name, dosage, hospital, bin number, expiration dates, NDC, UPC, GS1 barcode, location, patient or recipient information, recall information, use-by date, identifier for healthcare provider that is/was in possession of it, or the like. In some cases, the patient information system 120 stores the same medication data fields for each pharmacy item for which it stores data. For example, for each pharmacy item, the patient information system 120 can store one or more medication data field values for each medication data field it includes. However, in some cases, the patient information system 120 stores the different medication data fields for different pharmacy items.

Each medication data field can include one or more medication data field values. For example, a medication data field can include medication data field values for a plurality of pharmacy items. As an example, a medication data field "drug name" can include medication data field values of "Tylenol," "Propofol," "Fentanyl," etc.

In some cases, the patient information system 120 stores a limited number or particular set of medication data fields. The particular set of medication data fields that the patient information system 120 stores can be based on any number of factors including, but not limited to, the capabilities of the patient information system 120, its manufacturer, version, or the data available to the patient information system 120. For example, capabilities of the patient information system 120 may limit the categories, amount, types, etc. of information that the patient information system 120 can receive, store, and/or process. As a non-limiting example, in some cases, capabilities of the patient information system 120 may limit it to receiving, storing, or processing NDC numbers. In some such cases, communicating medication data field values that do not correspond to the medication data field of "NDC number" may be ignored, discarded, cause an error, etc.

The intercept device 130 can form part of the patient information system 120 or the scanning device 110, or can be located along the communication pathway between the patient information system 120 and the scanning device 110. The intercept device 130 can be configured with computer-executable instructions to receive or intercept the machine-readable data extracted from the machine-readable code or label, for example before any data is provided to the patient information system 120. The intercept device 130 can be configured with computer-executable instructions to parse the machine-readable data.

The intercept device 130 can identify which medication data fields that the patient information system 120 uses to store medication data field values. This can be accomplished using any of various techniques. For example, the intercept device 130 can query the patient information system 120 to request an indication of the medication data fields is uses. In some instances, the intercept device 130 can query the patient information system 120 by providing the patient information system 120 with the unique identifier. In response to the query, or in some cases without receiving the query, the patient information system 120 can communicate an indication of the categories it uses.

As another example, the intercept device 130 may be able to consult a lookup table to identify which medication data fields that the patient information system 120 uses to store medication data field values. For example, the intercept device 130 may have previously communicated with the patient information system 120, identified the categories, and stored an indication of the categories in a lookup table or other storage.

The intercept device 130 can identify the medication data fields that the patient information system 120 uses, or is configured use, to store data at any time, such as before, after, or while concurrently receiving the machine-readable data from the scanning device 110. For example, the intercept device 130 can be configured to determine the medication data fields or medication data field values accepted by the patient information system 120 as part of a set up procedure and/or prior to the scanning device 110 performing a scan.

The intercept device 130 can communicate a request to the tracking system 140 for the medication data field values that correspond to the medication data fields that the intercept device identified as being used by the patient information system 120. The request to the tracking system 140 can include an identifier of the medication data fields and a pharmacy item identifier. For example, the request can include some or all of the machine-readable data, such as a unique identifier, that the intercept device 130 receives from the scanning device 110. The intercept device 130 can relay the medication data field values received from the tracking system 140 to the patient information system 120. In addition or alternatively, the intercept device 130 can instruct the tracking system 140 to communicate the medication data field values to the patient information system 120.

As an example, if the intercept device 130 determines that the patient information system 120 uses only three medication data fields (for example, NDC, drug name, and expiration date), then the intercept device 130 can determine to query the tracking system 140 for medication data field values that correspond to at least those (or, in some cases, only those) three medication data fields. As a corollary, if the intercept device 130 determines that the patient information system 120 does not include a medication data field corresponding to expiration date, then the intercept device 130 can determine not to query the tracking system 140 for medication data field values that correspond to the expiration date. In this way, the intercept device 130 can dynamically determine which medication data fields that the patient information system 120 uses, thereby identifying which data to communicate to the patient information system 120 or which information to refrain from communicating to the patient information system 120.

The tracking system 140 can include information linking individual items with corresponding generic identifiers. For example, the tracking system 140 may include entries that relate a particular medication to its corresponding NDC or the tracking system 140 may include a tracking database 142 or NDC database. As another example, the tracking system 140 can include entries that relate the trade items with corresponding UPCs, GS1 barcodes, etc. The tracking system 140, the intercept device 130, or the patient information system 120 can be communicatively coupled to a generic identifier database, such as an NDC database.

In some instances, the tracking system 140 is separate from the intercept device 130. In some instances, the intercept device 130, and the tracking system 140 can be integrated into a single device. In some instances, the tracking system 140 is remotely located from the intercept device 130 or the other components in the environment 100. In some instances, the tracking system 140 is locally located relative to the intercept device 130 or the other components in the environment 100.

The tracking system 140 can use the request received from the intercept device 130 to update entries in the tracking database 142 or verify information related to the item. For example, the tracking system 140 can identify the unique identifier from the request and can track an item using the unique identifier.

The tracking system 140 can use the request received from the intercept device 130 to select medication data field values that both correspond to the particular pharmacy item associated with the unique identifier and correspond to the medication data fields identified as being used by the patient information system 120. For example, based on the request from the intercept device 130, the tracking system 140 can identify data corresponding to one or more entries in the tracking database 142.

The tracking system 140 can be configured to perform verifications. For example, where the item includes a medication to be administered to a patient, the tracking system 140 may verify that the particular medication is safe to be administered to a patient. For example, the tracking system 140 may verify pharmacy items by checking for expired or soon-to-be expired medications (for example, based on manufacturer's expiration date or other beyond-use dates), checking for recalled (or otherwise blacklisted) medications, etc. In some instances, when the tracking system 140 indicates that the particular medication is not safe to be administered to the patient, (for example, if the patient is allergic to the medication), the tracking system 140 can provide a notification (for example, an alarm) that the medication should not be administered.

The scanning device 110, intercept device 130, and tracking system 140 can be used together, to track items at various preparation, transport, or other processing stages. Additionally, in some instances, the intercept device 130 and the tracking system 140 can be integrated into existing systems. For example, where a facility already includes scanning devices 110 which are configured to communicate with the patient information systems 120, an intercept device 130 and tracking system 140 as described herein can be integrated into the existing system and provide additional functionality.

In some cases, the intercept device 130 and/or tracking system 140 are integrated into the patient information system 120. For instance, the intercept device 130 can include software that is running on the patient information system 120, for example, along with EMR software, and can intercept some or all keystrokes of the patient information system 120 and analyzes them. The scanning device 110 can scan the machine readable code of the pharmacy item and can communicate the machine readable data as keystrokes, for example, since barcode readers can imitate a keyboard.

The scanning device 110 can imitate or correspond to a keyboard and the intercept device 130 can intercept or receive the "keystrokes" corresponding to that keyboard. The intercept device 130 can identify keystrokes received by the patient information system 120. For example, if the intercept device 130 determines that the keystrokes correspond to regular typing, the intercept device 130 can pass those keystrokes along to whatever application has focus and is listening for them. This would allow, for example, a doctor to type notes in a patient's record. Alternatively, if the intercept device 130 determines that the keystrokes correspond to a unique identifier, then the intercept device 130 can capture the keystroke sequence. In some cases, the intercept device 130 can prevent the keystrokes events from passing to another application running on the patient information system 120. The intercept device 130 can look up the unique identifier, for example by communicating the unique identifier to the tracking database 142 of the tracking system 140.

In some cases, the intercept device 130 or the tracking system 140 can identify or determine a generic identifier (for example, a GTIN including the NDC) associated with the unique identifier, and can communicate a sequence of keystrokes to the focus application (for example, the EMR) on the patient information system 120 imitating those keystrokes. In some cases, rather than, or in addition to, identifying a generic identifier, the intercept device 130 or the tracking system 140 can determine types of data that the patient information system 120 is capable of accepting, and can provide the patient information system 120 with pharmacy item data corresponding to those types of data.

In some cases, the intercept device 130 and/or tracking system 140 can be integrated into, or run on, the scanning device 110. In some such cases, the intercept device 130 or the tracking system 140 can identify or determine the sequence of keystrokes associated with a unique or generic identifier, and can communicate those keystrokes to the patient information system 120. The patient information system 120 can interpret the keystrokes as a regular barcode scan, for example.

Example Data Flow Diagram

Figure 2:
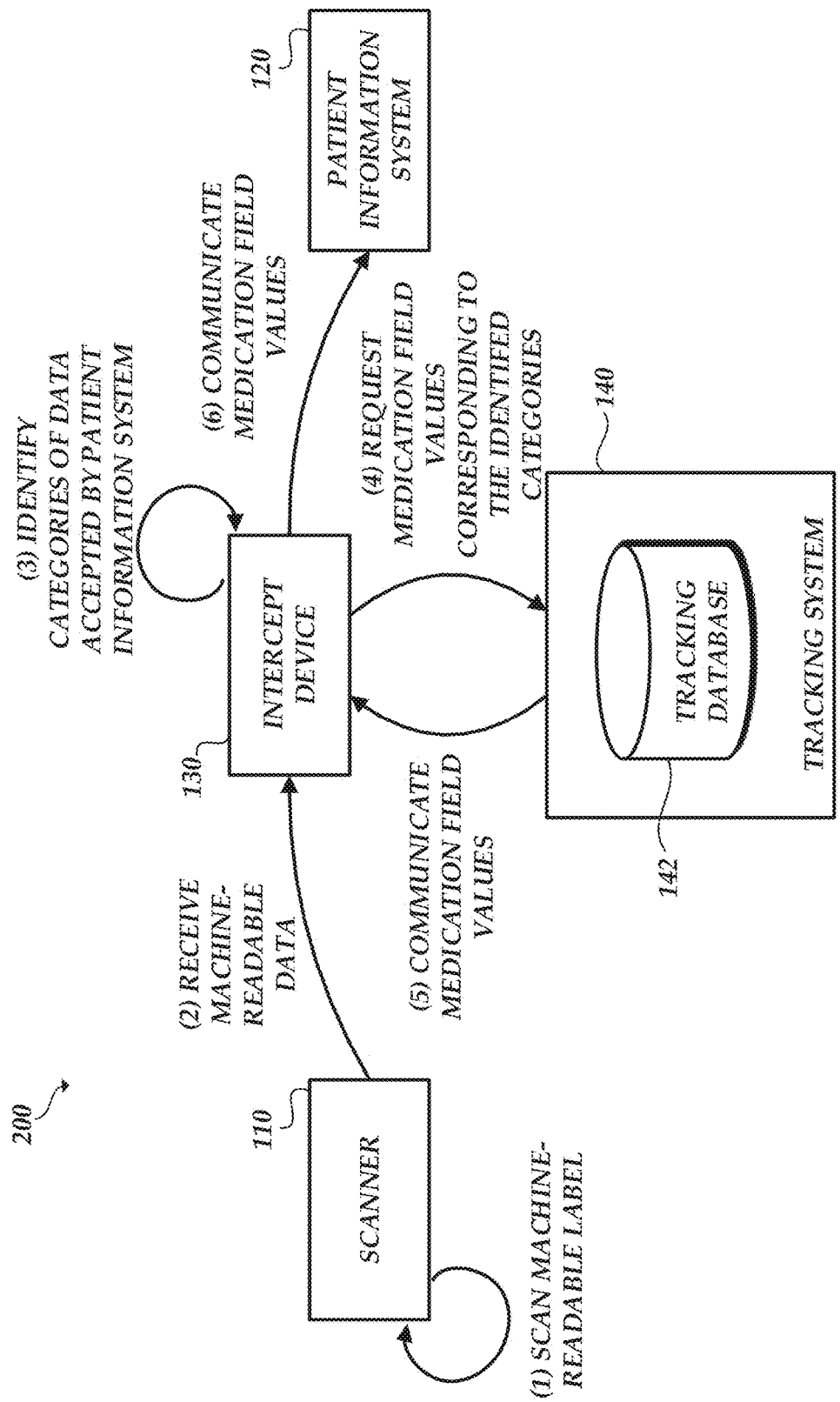
FIG. 2 illustrates is a data flow diagram illustrative of an example process for selectively distributing medication data field values to a patient information system.

FIG. 2 illustrates is a data flow diagram 200 illustrative of an example process for selectively distributing medication data field values to a patient information system 120. Although FIG. 2 only shows interactions between the scanning device 110, patient information system 120, intercept device 130, and tracking system 140, the environment 200 can include fewer or more components as desired, or can be configured differently. For example, additional communications can occur between any of the scanning device 110, patient information system 120, intercept device 130, and tracking system 140, or additional components can be used for communication.

At (1), the scanning device 110 scans one or more machine-readable codes, labels, or tags and retrieves machine-readable data. As described herein, the machine-readable data can include any type of data, such as a unique identifier, a generic identifier, a National Drug Code (NDC), a Universal Product Number (UPC), patient data, drug data, or the like. The machine-readable data can correspond to a particular medication or item, a particular type of medication, a particular dose of a medication, a particular patient, a particular healthcare professional, a particular location, or the like. The scanning device 110 can communicate at least some of the machine-readable data after the scan.

At (2), the intercept device 130 receives the machine-readable data. The intercept device 130 can receive the machine-readable data from the scanning device 110 or the patient information system 120. In some cases, the intercept device 130 intercepts the machine-readable data from communications between the scanning device 110 and the patient information system 120. The intercept device 130 can receive the machine-readable data from the scanning device 110 via a local bus, such as when the intercept device 130 and the scanning device 110 form part of a single device or via a network, such as when the intercept device 130 and the scanning device 110 are distinct devices.

The intercept device 130 can be configured with computer-executable instructions to parse the machine-readable data, for example, to extract or determine the unique identifier. For example, the unique identifiers can be embedded into machine-readable codes or labels. In addition or alternatively, the machine-readable data can be the unique identifier. In some cases, the intercept device 130 can generate the unique identifier, for example, based on the machine-readable data received from the scanning device 110. For instance, the intercept device 130 can associate unique identifiers with items based on the machine-readable data.

At (3), the intercept device 130 identifies the categories of data that the patient information system 120 uses to store data. As described herein, the patient information system 120 can include a database that stores multiple categories of data for various pharmacy items. The categories, which can be referred to as medication data fields, can include, but are not limited to, drug name, dosage, hospital, bin number, expiration dates, NDC, UPC, GS1 barcode, location, patient or recipient information, recall information, use-by date, or the like. In some cases, the patient information system 120 stores the same categories of data for each pharmacy item on which it stores data. For example, for each pharmacy item, the patient information system 120 can store one or more values (generally referred to as medication data field values) for each category of data that it stores. In some cases, the patient information system 120 stores the different categories of data for different pharmacy items. In some such cases, the intercept device 130 can identify the medication data fields that the patient information system 120 is uses to store medication data field values for the pharmacy item that corresponds to the unique identifier.

The intercept device 130 can identify the categories of data that the patient information system 120 is uses to store data using any of various techniques. For example, the intercept device 130 can query the patient information system 120 to request an indication of the categories. In some instances, the intercept device 130 can query the patient information system 120 by providing the patient information system 120 with the unique identifier. In response to the query, or in some cases without receiving the query, the patient information system 120 can communicate an indication of the categories it uses. As another example, to identify the categories the intercept device 130 can consult a lookup table. For example, the intercept device 130 may have previously communicated with the patient information system 120, identified the categories, and stored an indication of the categories in a lookup table or other storage.

At (4), the intercept device 130 communicates a request for medication data field values that correspond to the categories identified at step (3) to the tracking system 140. The request can identify the pharmacy item that corresponds to the unique identifier. For example, the request can include the unique identifier or other indication of the pharmacy item. In some cases, the request can indicate the categories identified at step (3). In some cases, the request may not indicate the categories. For example, the intercept device 130 can be configured to filter out or ignore any medication data field values received from the tracking system 140 that do not correspond to the categories identified at step (3).

The intercept device 130 can communicate the request to the tracking system 140 via a local bus, such as when the intercept device 130 and the tracking system 140 form part of a single device or via a network, such as when the intercept device 130 and the tracking system 140 are distinct devices.

At (5), the tracking system 140 communicates medication data field values to the intercept device 130. The tracking system 140 can receive the request from the intercept device 130 and can identify the medication data field values based on the request. For example, the tracking system 140 can identify those medication data field values that correspond to the unique identifier and correspond to the medication data field used by the patient information system 120. In some cases, the tracking database 142 can use the unique identifier to identify a generic identifier that corresponds to the unique identifier. The generic identifier can be used by the patient information system 120 to obtain additional data from another database, such as an NDC database.

At (6), the intercept device 130 communicates at least some of the medication data field values it received at step (5) to the patient information system 120. In some cases, the intercept device 130 communicates only medication data field values that it has determined are used by the patient information system 120.

In some cases, the intercept device 130 communicates at least one medication data field value that corresponds to a medication data field that the patient information system 120 does not use. In one such cases, the patient information system 120 may discard or ignore those medication data field values as superfluous. In this way, the patient information system 120 can filter or select the medication data field values that correspond to medication data fields that the patient information system 120 uses. In some cases, the patient information system 120 may expand its database to include one or more additional medication data fields so that it can store the those additional medication data field values.

As a non-limiting example, if the intercept device 130 determines that the patient information system 120 includes medication data fields for UPC and drug name, but does not include a medication data field for expiration date, then the intercept device 130 may selectively request medication data field values for UPC and drug name from the remotely located database, without making a request for medication data field values corresponding to expiration date.

In certain embodiments, any interactions (1)-(6) may be omitted, occur concurrently, or occur in a different order, as desired. For example, the intercept device 130 can identify the categories of data accepted by the patient information system 120 prior to, or concurrently with, any of interactions (1) or (2). Furthermore, it will be understood that fewer, more, or different interactions may occur as part of the data flow diagram 200. For example, in some cases, the tracking system 140 can update or create database entries associated with the pharmacy item in the tracking database 142 to indicate that the pharmacy item has reached a particular location, has been placed in the custody of a particular person, or has entered or completed a particular processing step. For instance, the tracking system 140 can use the request to update or create database entry indicating that a dose is being administered to the patient.

As another example, in some cases, the tracking system 140 can verify the particular item based on the request. For example, the unique identifier can be used to ensure that a particular pharmacy item or dose of a pharmacy item is at a correct location within a healthcare facility (for example, at a correct nursing station in route to a patient or in the proper patient's hospital room), that custody of the pharmacy item or dose of a pharmacy item has been given to a proper healthcare professional, (for example, a nurse assigned to the particular patient for whom the pharmacy item has been prepared), that any timing requirements associated with the pharmacy item or dose of a pharmacy item are met, (for example, ensure that medications are timely administered to the patient), that the pharmacy item or dose of a pharmacy item is administered to the correct patient, or that the pharmacy item or dose of a pharmacy item is safe for administration to the patient, (for example, by checking expiration dates, beyond use dates, and blacklist/recall statuses). Other verifications can also be performed.

As another example, the intercept device 130 or the tracking system 140 one or more safety and inventory checks. For instance, the intercept device 130 or the tracking system 140 can verify whether the medication corresponding to the pharmacy item 302 may be expired, have exceeded it's beyond use dating, or be flagged as a recalled/blacklisted item. In some cases, if the intercept device 130 or the tracking system 140 determines one or more safety and inventory check errors, the intercept device 130 or the tracking system 140 can cause an alert, for example to the patient or caregiver, or prevent an action, for example by not passes the keystrokes on to another application (e.g., an EMR) of the patient information system 120.

Flow Diagram

Figure 3:
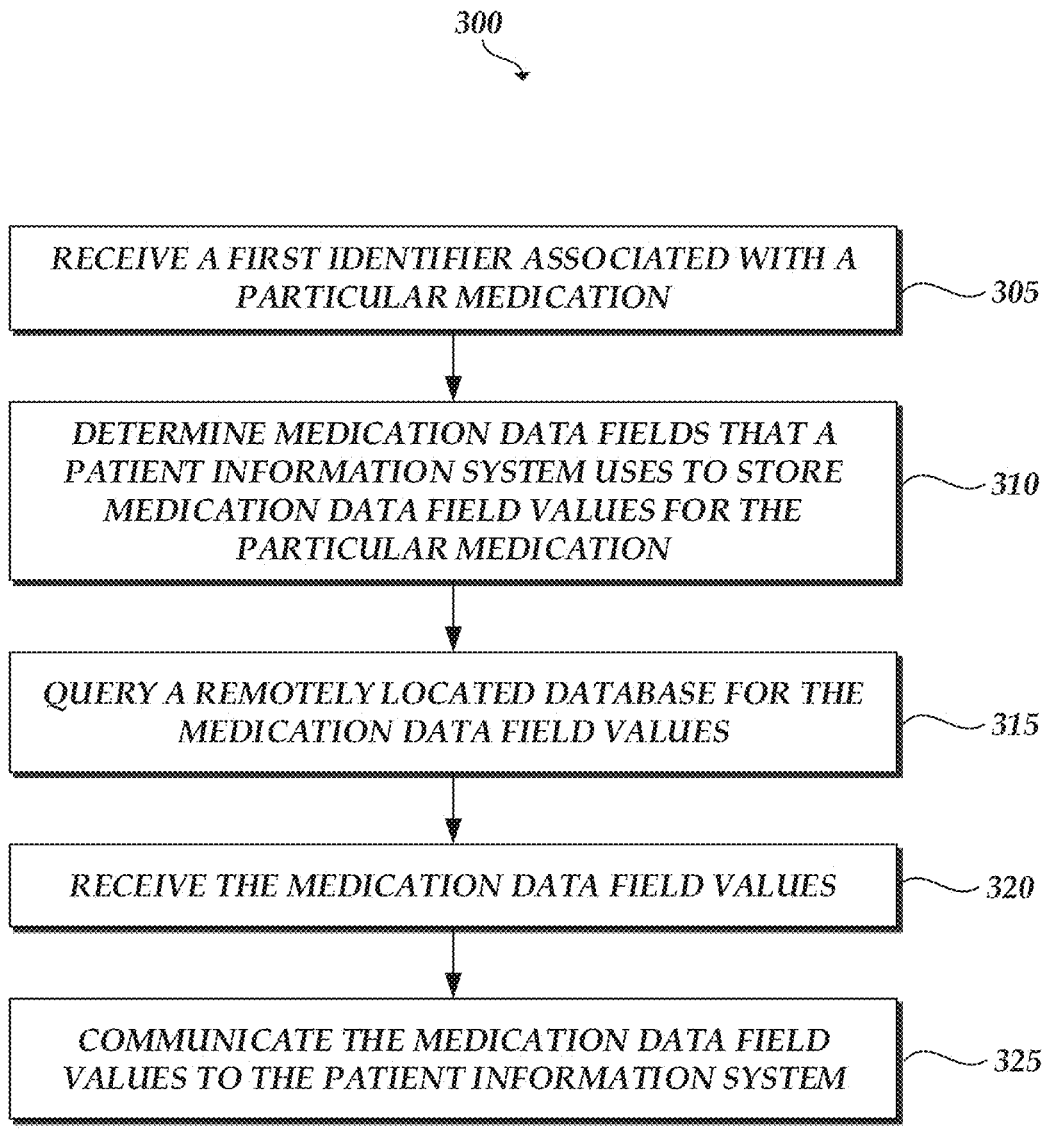
FIG. 3 is a flow diagram illustrating an embodiment of a routine for selectively communicating medication data field values based on the medication data fields that a patient information system uses to store data.

FIG. 3 is a flow diagram illustrating an embodiment of a routine 300 for selectively communicating medication data field values based on the medication data fields that a patient information system 120 uses to store data. In this way, the intercept device 130 can provide varying levels of detail about a pharmacy item to the patient information system based on the capabilities or configuration of the patient information system 120. One skilled in the relevant art will appreciate that the elements outlined for routine 300 can be implemented by one or more computing devices that are associated with the environment 100, including, but not limited to, the scanning device 110, the patient information system 120, the intercept device 130, the tracking system 140, or any combination thereof. For simplicity, routine 300 has been associated as being generally performed by the intercept device 130. However, the following illustrative embodiments should not be construed as limiting.

At block 305, the intercept device 130 receives an identifier. The identifier can be part of machine-readable data retrieved by a scanning device 110 after it scans one or more machine-readable codes, labels, or tags. In some cases, the intercept device 130 receives the identifier, or the machine-readable data including the identifier, as part of communications from the scanning device 110 to the intercept device 130. In some cases, the intercept device 130 receives the identifier by intercepting communications between the scanning device 110 and the patient information system 120. As described, the can correspond to, among other things, a particular drug, a particular type of drug, a particular medicinal container including a particular drug, or a particular medical container including a particular type of drug. Further, the identifier can uniquely identify a medicinal container from other medicinal containers that include the same drug or same type of drug or can uniquely identify a medicinal container from all other medicinal containers.

At block 310, the intercept device 130 determines one or more medication data fields that a patient information system 120 uses to store data. As described herein, the patient information system 120 can include a database, such as a database for electronic medical records (EMRs), and the database can use a particular set of medication data fields for storing medication data field values. In some cases, the patient information system 120 uses the same medication data fields for each item. In some cases, the patient information system 120 may use different same medication data fields for different items. In some such cases, the intercept device 130 can determine the one or more medication data fields that the patient information system uses to store medication data field values for the particular item that corresponds to the unique identifier.

The intercept device 130 may determine the one or more medication data fields that a patient information system 120 uses to store data using any of various techniques. For example, the intercept device 130 can query the patient information system 120 to request an indication of the one or more medication data fields. In some instances, the intercept device 130 can query the patient information system 120 by providing the patient information system 120 with the unique identifier. In response, the patient information system 120 can communicate an indication of the medication data fields it uses to store data, such as the more medication data fields it uses to store medication data field values for the particular item that corresponds to the unique identifier.

As another example, the intercept device 130 can consult a lookup table to determine the medication data fields. For example, the intercept device 130 may have previously communicated with the patient information system 120 and may already know which medication data fields the patient information system 120 uses to store data and/or is capable of receive.

The intercept device 130 can identify the medication data fields that the patient information system 120 uses, or is configured use, to store data at any time, such as before, after, or while concurrently receiving the machine-readable data from the scanning device 110. For example, the intercept device 130 can be configured to determine the medication data fields or medication data field values accepted by the patient information system 120 as part of a set up procedure and/or prior to the scanning device 110 performing a scan.

At block 315, the intercept device 130 queries a remotely located database for one or more medication data field values associated with the one or more medication data fields determined at block 310. In some cases, the data is stored locally.

As a non-limiting example, the remotely located database may include medication data fields for UPC, drug name, and expiration date. If the intercept device 130 determines that the patient information system 120 includes medication data fields for UPC and drug name, but does not include a medication data field for expiration date, then the intercept device 130 may selectively request medication data field values for UPC and drug name from the remotely located database, without making a request for medication data field values corresponding to expiration date.

In some cases, the intercept device 130 may request and/or the remotely located database may communicate medication data field values that do not correspond to medication data fields that the patient information system 120 uses or is configured to use. In some such cases, the intercept device 130 may discard or ignore those medication data field values as superfluous. In this way, the intercept device 130 can filter the medication data field values that correspond to medication data fields that the patient information system 120.

At block 320, the intercept device 130 receives one or more medication data field values corresponding to the query. In some cases, the intercept device 130 may receive medication data field values that do not correspond to medication data fields that the patient information system 120 uses or is configured to use. In some such cases, the intercept device 130 may discard or ignore those medication data field values as superfluous. In this way, the intercept device 130 can filter or select the medication data field values that correspond to medication data fields that the patient information system 120 uses.

At block 325, the intercept device 130 communicates the one or more medication data field values to the patient information system 120. In some cases, the intercept device 130 may communicate medication data field values that do not correspond to medication data fields that the patient information system 120 uses or is configured to use. In some such cases, the patient information system 120 may discard or ignore those medication data field values as superfluous. In this way, the patient information system 120 can filter or select the medication data field values that correspond to medication data fields that the patient information system 120 uses.

It will be understood that the various blocks described herein can be implemented in a variety of orders, and that the intercept device 130 can implement one or more of the blocks concurrently and/or change the order, as desired. For example, the intercept device 130 determine that medication data fields that the patient information system uses prior to, or concurrently with, receiving the identifier. Furthermore, it will be understood that fewer, more, or different blocks can be used as part of the routine 800. For example, the routine 1600 can include blocks for querying the patient information system 120 to determine which medicate data fields it uses.

Example Embodiments

Various examples of methods and systems for selectively communicating medication data field values to a patient information system can be found in the following clauses:

Clause 1. A method comprising:
receiving, from a scanning device, a first identifier corresponding to a computer-readable code associated with a medicinal container including a particular medication, wherein the first identifier uniquely identifies the medicinal container from other medicinal containers;
determining one or more medication data fields that a patient information system uses to store one or more medication data field values for the particular medication, wherein the patient information system is communicatively coupled with the scanning device;
querying, based at least in part on the first identifier, a remotely located database for the one or more medication data field values for the particular medication;
receiving the one or more medication data field values for the particular medication; and
communicating the one or more medication data field values to the patient information system.

Clause 2. The method of clause 1, wherein the first identifier uniquely identifies the medicinal container from other medicinal containers that include the same type of drug.

Clause 3. The method of any of the previous clauses, wherein the first identifier uniquely identifies the medicinal container from other medicinal containers that include the same drug.

Clause 4. The method of any of the previous clauses, wherein the scanning device comprises an RFID reader.

Clause 5. The method of any of the previous clauses, wherein the scanning device comprises a barcode scanner.

Clause 6. The method of clause 5, wherein the computer-readable code is a one-dimensional barcode or a two-dimensional barcode.

Clause 7. The method of any of the previous clauses, wherein said querying the remotely located database comprises transmitting the first identifier to a remotely-located tracking system.

Clause 8. The method of clause 7, wherein the remotely-located tracking system is configured to:
identify the one or more medication data field values for the particular medication based at least in part on the first identifier, and
communicate the one or more medication data field values.

Clause 9. The method of any of the previous clauses, wherein said determining one or more medication data fields comprises querying the patient information system database for the one or more medication data fields.

Clause 10. The method of any of Clauses 7-9, wherein the remotely-located tracking system is configured to update location information associated with the particular medication.

Clause 11. The method of any of the previous clauses, wherein the medication data field values comprise an NDC number.

Clause 12. The method of any of the previous clauses, wherein the medication data field values comprise a name of the particular drug.

Clause 13. The method of any of the previous clauses, wherein the medication data field values comprise recall information.

Clause 14. The method of any of the previous clauses, wherein the medication data field values comprise at least one of a use-by date or an expiration date.

Clause 15. The method of any of the previous clauses, wherein the patient information system is an electronic medical records database.

Clause 16. A system comprising:
an intercept device communicatively coupled along a communication pathway between a scanning device and a patient information system, the intercept device comprising a processor configured to:
receive, from the scanning device, a first identifier corresponding to a computer-readable code associated with a medicinal container including a particular medication, wherein the first identifier uniquely identifies the medicinal container from other medicinal containers;
determine one or more medication data fields that the patient information system uses to store one or more medication data field values for the particular medication, wherein the patient information system is communicatively coupled with the scanning device;
query, based at least in part on the first identifier, a remotely located database for the one or more medication data field values for the particular medication;
receive the one or more medication data field values for the particular medication; and
communicate the one or more medication data field values to the patient information system.

Clause 17. The system of clause 16, wherein the first identifier uniquely identifies the medicinal container from other medicinal containers that include the same type of drug.

Clause 18. The system of any of clauses 16 or 17, wherein the first identifier uniquely identifies the medicinal container from other medicinal containers that include the same drug.

Clause 19. The system of any of clauses 16 to 18, wherein the scanning device comprises an RFID reader.

Clause 20. The system of any of clauses 16 to 19, wherein the scanning device comprises a barcode scanner.

Clause 21. The system of clause 20, wherein the computer-readable code is a one-dimensional barcode or a two-dimensional barcode.

Clause 22. The system of any of clauses 16 to 21, wherein said querying the remotely located database comprises transmitting the first identifier to a remotely-located tracking system.

Clause 23. The system of clause 22, wherein the remotely-located tracking system is configured to:
identify the one or more medication data field values for the particular medication based at least in part on the first identifier, and
communicate the one or more medication data field values.

Clause 24. The system of clause 22, wherein to determine the one or more medication data fields, the intercept device is configured to query the patient information system database for the one or more medication data fields.

Clause 25. The system of clause 22, wherein the remotely-located tracking system is configured to update location information associated with the particular medication.

Clause 26. The system of any of clauses 16 to 25, wherein the medication data field values comprise an NDC number.

Clause 27. The system of any of clauses 16 to 26, wherein the medication data field values comprise a name of the particular drug.

Clause 28. The system of any of clauses 16 to 27, wherein the medication data field values comprise recall information.

Clause 29. The system of any of clauses 16 to 28, wherein the medication data field values comprise at least one of a use-by date or an expiration date.

Clause 30. The system of any of clauses 16 to 29, wherein the patient information system is an electronic medical records database.

Clause 31. The system of any of clauses 16 to 30, wherein to receive the first identifier, the intercept device is configured to intercept a communication from the scanning device to the patient information system.

Clause 32. The system of any of clauses 16 to 31, wherein the remotely located database stores medication data field values associated with a plurality of medication data fields, wherein the one or more medication data fields that the patient information system uses to store the one or more medication data field values for the particular medication includes some but not all of the plurality of medication data fields.

ADDITIONAL CONSIDERATIONS

Conjunctive language such as the phrase "at least one of X, Y and Z," unless specifically stated otherwise, is otherwise understood with the context as used in general to convey that an item, term, etc. may be either X, Y or Z. Thus, such conjunctive language is not generally intended to imply that certain embodiments require at least one of X, at least one of Y and at least one of Z to each be present.

Conditional language, such as, among others, "can," "could," "might," or "can," unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above detailed description using the singular or plural number can also include the plural or singular number respectively. The word "or" in reference to a list of two or more items, covers all of the following interpretations of the word: any one of the items in the list, all of the items in the list, and any combination of the items in the list. Likewise, the term "and/or" in reference to a list of two or more items, covers all of the following interpretations of the word: any one of the items in the list, all of the items in the list, and any combination of the items in the list.

Depending on the embodiment, certain operations, acts, events, or functions of any of the algorithms described herein can be performed in a different sequence, can be added, merged, or left out altogether (for example, not all are necessary for the practice of the algorithms). Moreover, in certain embodiments, operations, acts, functions, or events can be performed concurrently, for example, through multi-threaded processing, interrupt processing, or multiple processors or processor cores or on other parallel architectures, rather than sequentially.

Systems and modules described herein can comprise software, firmware, hardware, or any combination(s) of software, firmware, or hardware suitable for the purposes described herein. Software and other modules can reside and execute on servers, workstations, personal computers, computerized tablets, PDAs, and other computing devices suitable for the purposes described herein. Software and other modules can be accessible via local memory, via a network, via a browser, or via other means suitable for the purposes described herein. Data structures described herein can comprise computer files, variables, programming arrays, programming structures, or any electronic information storage schemes or methods, or any combinations thereof, suitable for the purposes described herein. User interface elements described herein can comprise elements from graphical user interfaces, interactive voice response, command line interfaces, and other suitable interfaces.

Further, the processing of the various components of the illustrated systems can be distributed across multiple machines, networks, and other computing resources. In addition, two or more components of a system can be combined into fewer components. Various components of the illustrated systems can be implemented in one or more virtual machines, rather than in dedicated computer hardware systems and/or computing devices. Likewise, the data storage devices shown can represent physical and/or logical data storage, including, for example, storage area networks or other distributed storage systems. Moreover, the connections between the components shown can represent possible paths of data flow, rather than actual connections between hardware. While some examples of possible connections are shown, any of the subset of the components shown can communicate with any other subset of components in various implementations.

Embodiments are also described above with reference to flow chart illustrations and/or block diagrams of methods, apparatus (systems) and computer program products. Each block of the flow chart illustrations and/or block diagrams, and combinations of blocks in the flow chart illustrations and/or block diagrams, can be implemented by computer program instructions. Such instructions can be provided to a processor of a general purpose computer, special purpose computer, specially-equipped computer (for example, comprising a high-performance database server, a graphics subsystem, etc.) or other programmable data processing apparatus to produce a machine, such that the instructions, which execute via the processor(s) of the computer or other programmable data processing apparatus, create means for implementing the acts specified in the flow chart and/or block diagram block or blocks.

These computer program instructions can also be stored in a non-transitory computer-readable memory that can direct a computer or other programmable data processing apparatus to operate in a particular manner, such that the instructions stored in the computer-readable memory produce an article of manufacture including instruction means which implement the acts specified in the flow chart and/or block diagram block or blocks. The computer program instructions can also be loaded onto a computing device or other programmable data processing apparatus to cause a series of operations to be performed on the computing device or other programmable apparatus to produce a computer implemented process such that the instructions which execute on the computer or other programmable apparatus provide steps for implementing the acts specified in the flow chart and/or block diagram block or blocks.

Any patents and applications and other references noted above, including any that can be listed in accompanying filing papers, are incorporated herein by reference. Aspects of the disclosure can be modified, if necessary, to employ the systems, functions, and concepts of the various references described above to provide yet further implementations of the disclosure.

These and other changes can be made in light of the above detailed description. While the above description describes certain examples of the disclosure, and describes the best mode contemplated, no matter how detailed the above appears in text, the disclosure can be practiced in many ways. Details of the system can vary considerably in its specific implementation, while still being encompassed by the disclosure disclosed herein. As noted above, particular terminology used when describing certain features or aspects of the disclosure should not be taken to imply that the terminology is being redefined herein to be restricted to any specific characteristics, features, or aspects of the disclosure with which that terminology is associated. In general, the terms used in the following claims should not be construed to limit the disclosure to the specific examples disclosed in the specification, unless the above detailed description section explicitly defines such terms. Accordingly, the actual scope of the disclosure encompasses not only the disclosed examples, but also all equivalent ways of practicing or implementing the disclosure under the claims.

What is claimed is:

1. A method comprising:
  receiving, from a scanning device, a first identifier corresponding to a computer-readable code associated with a pharmacy item container including a particular pharmacy item, wherein the first identifier uniquely identifies the pharmacy item container from other pharmacy item containers that include the particular pharmacy item and a same amount of the particular pharmacy item as the pharmacy item container;

determining a first set of data fields that a patient information system uses to store a corresponding first set of data field values for the particular pharmacy item, wherein the patient information system is communicatively coupled with the scanning device;

querying, based at least in part on the first identifier, a remotely located database for the first set of data field values for the particular pharmacy item, wherein the remotely located database stores a second set of data fields associated with the pharmacy item container and a corresponding second set of data field values, wherein the first set of data field values is a subset of the second set of data field values;

receiving the first set of data field values for the particular pharmacy item; and communicating the first set of data field values to the patient information system.

2. The method of claim 1, wherein the scanning device comprises an RFID reader.

3. The method of claim 1, wherein the scanning device comprises a barcode scanner.

4. The method of claim 3, wherein the computer-readable code is a one-dimensional barcode or a two-dimensional barcode.

5. The method of claim 1, wherein querying the remotely located database comprises transmitting the first identifier to a remotely-located tracking system.

6. The method of claim 5, wherein the remotely-located tracking system is configured to:
identify the first set of data field values for the particular pharmacy item based at least in part on the first identifier, and
communicate the first set of data field values.

7. The method of claim 5, wherein the remotely-located tracking system is configured to update location information associated with the particular pharmacy item.

8. The method of claim 1, wherein determining the first set of data fields comprises querying the remotely located database for the first set of data fields.

9. The method of claim 1, wherein the first set of data field values or the second set of data field values comprise an NDC number.

10. The method of claim 1, wherein the first set of data field values or the second set of data field values comprise a name of the particular pharmacy item.

11. The method of claim 1, wherein the first set of data field values or the second set of data field values comprise recall information.

12. The method of claim 1, wherein the first set of data field values or the second set of data field values comprise at least one of a use-by date or an expiration date.

13. The method of claim 1, wherein the patient information system is an electronic medical records database.

14. A system comprising:
an intercept device communicatively coupled along a communication pathway between a scanning device and a patient information system, the intercept device comprising one or more processors configured to:
receive, from the scanning device, a first identifier corresponding to a computer-readable code associated with a pharmacy item container including a particular pharmacy item, wherein the first identifier uniquely identifies the pharmacy item container from other pharmacy item containers that include the particular pharmacy item and a same amount of the particular pharmacy item as the pharmacy item container;

determine a first set of data fields that the patient information system uses to store a corresponding first set of data field values for the particular pharmacy item, wherein the patient information system is communicatively coupled with the scanning device;

query, based at least in part on the first identifier, a remotely located database for the first set of data field values for the particular pharmacy item, wherein the remotely located database stores a second set of data fields associated with the pharmacy item container and a corresponding second set of field values, wherein the first set of data field values is a subset of the second set of data field values;

receive the first set of data field values for the particular pharmacy item; and communicate the first set of data field values to the patient information system.

15. The system of claim 14, wherein the scanning device comprises at least one of an RFID reader or a barcode scanner.

16. The system of claim 14, wherein to determine the first set of data fields, the one or more processors are configured to query the remotely located database for the first set of data fields.

17. The system of claim 14, wherein the first set of data field values or the second set of data field values comprise at least one of an NDC number, a name of the particular pharmacy item, recall information, a use-by date, or an expiration date.

18. The system of claim 14, further comprising a second identifier remote from the first identifier and comprising information associated with a particular patient, wherein the one or more processors are further configured to correlate the first identifier and the second identifier to verify patient administration.

19. The system of claim 14, wherein to query the remotely located database the one or more processors are configured to transmit the first identifier to a remotely-located tracking system; and wherein the remotely-located tracking system is configured to:
identify the first set of data field values for the particular pharmacy item based at least in part on the first identifier, and
communicate the first set of data field values.

20. Non-transitory computer-readable media comprising computer-executable instructions that, when executed by a computing system for determining event discrepancies between data sets from distributed systems, cause the computing system to:
receive, from a scanning device, a first identifier corresponding to a computer-readable code associated with a pharmacy item container including a particular pharmacy item, wherein the first identifier uniquely identifies the pharmacy item container from other pharmacy item containers that include the particular pharmacy item and a same amount of the particular pharmacy item as the pharmacy item container;

determine a first set of data fields that a patient information system uses to store a corresponding first set of data field values for the particular pharmacy item, wherein the patient information system is communicatively coupled with the scanning device;

query, based at least in part on the first identifier, a remotely located database for the first set of data field values for the particular pharmacy item, wherein the remotely located database stores a second set of data fields associated with the pharmacy item container and a corresponding second set of data field values, wherein the first set of data field values is a subset of the second set of data field values;

receive the first set of data field values for the particular pharmacy item; and communicate the first set of data field values to the patient information system.

* * * * *